(12) United States Patent
Ramsey et al.

(10) Patent No.: US 11,345,947 B2
(45) Date of Patent: *May 31, 2022

(54) MICROFLUIDIC DEVICES, SOLID SUPPORTS FOR REAGENTS AND RELATED METHODS

(71) Applicant: The University of North Carolina at Chapel Hill, Chapel Hill, NC (US)

(72) Inventors: John Michael Ramsey, Chapel Hill, NC (US); William Henley, Chapel Hill, NC (US); Emily Oblath, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 380 days.

This patent is subject to a terminal disclaimer.

(21) Appl. No.: 15/445,217

(22) Filed: Feb. 28, 2017

(65) Prior Publication Data

US 2017/0233797 A1    Aug. 17, 2017

Related U.S. Application Data

(63) Continuation of application No. 14/402,565, filed as application No. PCT/US2013/032300 on Mar. 15, 2013, now Pat. No. 9,617,589.
(Continued)

(51) Int. Cl.
*C12Q 1/68* (2018.01)
*C12Q 1/6823* (2018.01)
(Continued)

(52) U.S. Cl.
CPC ...... *C12Q 1/6823* (2013.01); *B01L 3/502761* (2013.01); *B01L 7/52* (2013.01); *C12Q 1/686* (2013.01); *C12Q 1/6853* (2013.01); *B01J 2219/005* (2013.01); *B01J 2219/00317* (2013.01); *B01J 2219/00454* (2013.01);
(Continued)

(58) Field of Classification Search
CPC ...................................................... C12Q 1/68
See application file for complete search history.

(56) References Cited

U.S. PATENT DOCUMENTS

| 4,978,540 A | 12/1990 | Lee |
| 6,042,709 A | 3/2000 | Parce et al. |

(Continued)

FOREIGN PATENT DOCUMENTS

| CN | 1464071 | 12/2003 |
| CN | 101553306 | 10/2009 |

(Continued)

OTHER PUBLICATIONS

Quanterix, Scientific Principle of Simoa™ (Single Molecule Array) Technology, attached, Dec. 2013.*
(Continued)

*Primary Examiner* — Aaron A Priest
(74) *Attorney, Agent, or Firm* — Myers Bigel, P.A.

(57) ABSTRACT

A microfluidic device includes a plurality of reaction wells; and a plurality of solid supports, and each of the solid supports has a reagent attached thereto. The reagent is attached to the solid support via a labile reagent/support bond such that the reagent is configured to be cleaved from the support via a cleaving operation.

14 Claims, 15 Drawing Sheets

Related U.S. Application Data

(60) Provisional application No. 61/651,648, filed on May 25, 2012.

(51) Int. Cl.
  *B01L 7/00* (2006.01)
  *C12Q 1/6853* (2018.01)
  *B01L 3/00* (2006.01)
  *C12Q 1/686* (2018.01)
  *G01N 35/00* (2006.01)

(52) U.S. Cl.
  CPC .......... *B01J 2219/00495* (2013.01); *B01J 2219/00554* (2013.01); *B01J 2219/00576* (2013.01); *B01J 2219/00619* (2013.01); *B01L 3/5027* (2013.01); *B01L 3/502715* (2013.01); *B01L 2200/16* (2013.01); *B01L 2300/0636* (2013.01); *B01L 2300/0829* (2013.01); *B01L 2300/0864* (2013.01); *G01N 2035/00158* (2013.01)

(56) References Cited

U.S. PATENT DOCUMENTS

| | | | |
|---|---|---|---|
| 6,143,496 | A | 11/2000 | Brown et al. |
| 6,565,813 | B1 | 5/2003 | Garyantes |
| 6,589,779 | B1 | 7/2003 | McDevitt et al. |
| 8,222,047 | B2 | 7/2012 | Duffy et al. |
| 8,236,574 | B2 | 8/2012 | Duffy et al. |
| 8,846,415 | B2 | 9/2014 | Duffy et al. |
| 9,110,025 | B2 | 8/2015 | Rissin et al. |
| 2002/0102578 | A1 | 8/2002 | Dickinson |
| 2003/0049620 | A1 | 3/2003 | Lai |
| 2003/0082576 | A1 | 5/2003 | Jones et al. |
| 2004/0014168 | A1 | 1/2004 | Schreiber |
| 2005/0059048 | A1 | 3/2005 | Gunderson et al. |
| 2006/0088857 | A1 | 4/2006 | Attiya et al. |
| 2006/0228734 | A1* | 10/2006 | Vann ............... G01N 33/54386 435/6.19 |
| 2009/0032401 | A1* | 2/2009 | Ronaghi ........... B01L 3/502761 204/549 |
| 2009/0021401 | A1 | 5/2009 | Ronaghi et al. |
| 2009/0146380 | A1 | 6/2009 | Votaw et al. |
| 2010/0137143 | A1* | 6/2010 | Rothberg ............. C12Q 1/6874 506/2 |
| 2010/0184036 | A1 | 7/2010 | Fu |
| 2010/0248991 | A1* | 9/2010 | Roesler ............... C12Q 1/6844 506/16 |
| 2010/0255471 | A1 | 10/2010 | Clarke et al. |
| 2010/0317535 | A1 | 12/2010 | Schmidt et al. |
| 2011/0009275 | A1* | 1/2011 | Leamon ............... C12Q 1/6844 506/2 |
| 2012/0202709 | A1* | 8/2012 | Bergo ..................... C40B 30/10 506/12 |
| 2012/0322666 | A1* | 12/2012 | Pham ............... G01N 33/54313 506/2 |
| 2014/0323330 | A1 | 10/2014 | Bergo |
| 2015/0151298 | A1 | 6/2015 | Hobbs et al. |
| 2016/0223531 | A1* | 8/2016 | Noji ................. G01N 33/54386 |

FOREIGN PATENT DOCUMENTS

| | | |
|---|---|---|
| CN | 101848765 | 9/2010 |
| JP | 2002502955 | 1/2002 |
| JP | 2003-009890 | 1/2003 |
| JP | 2007525963 | 9/2007 |
| JP | 2010519896 | 6/2010 |
| WO | WO 91/11533 | 8/1991 |
| WO | WO 96/37630 | 11/1996 |
| WO | 99/39829 | 8/1999 |
| WO | WO 2005/071056 | 8/2005 |
| WO | 2007092713 | 8/2007 |
| WO | 20090078812 | 6/2009 |
| WO | WO 2012/055069 | 5/2012 |
| WO | WO 2013/188872 | 12/2013 |

OTHER PUBLICATIONS

Thermo, Instructions, Starting Block™ Blocking Buffers, attached, Dec. 2012.*
Definition of "immiscible," dictionary.com, available at https://www.dictionary.com/browse/immiscible, accessed Jan. 8, 2021.*
Berti et al. "Microfluidic-based electrochemical genosensor coupled to magnetic beads for hybridization detection", Talanta, 77:971-978 (2009).
Chinese Office Action corresponding to Application No. 201380039315 dated Oct. 10, 2015, 8 pages.
Dörre et al. "Techniques for single molecule sequencing", *Bioimaging*, 5 (1997), pp. 139-152.
European Search Report Corresponding to European Application No. 13 794 324.7; dated: Mar. 1, 2016; 10 Pages.
Handique et al. "Microfluidic flow control using selective hydrophobic patterning", SPIE, vol. 3224, Jan. 1997, 185-195.
Henley et al. "Fabrication of Microfluidic Devices Containing Patterned Microwell Arrays", Analytical Chemistry, (2012), 84, 1776-1780.
Hinz et al. "Polymer support for exonucleolytic sequencing", *Journal of Biotechnology*, 86 (2001), pp. 281-288.
Holmberg et al., "The biotin-streptavidin interaction can be reversibly broken using water at elevated temperatures", Electrophoresis, 2005, vol. 26, pp. 501-510.
Huang et al. "Highly sensitive mutation detection based on digital amplification coupled with hydrogel bead-array", *Chem. Commun., The Royal Society of Chemistry*, 2009, pp. 4094-4096.
International Search Report and Written Opinion for PCT/US2013/032300 dated Jul. 10, 2013.
Kan et al., "Isolation and Detection of Single Molecules on Paramagnetic Beads Using Sequential fluid Flows in Microfabricated Polymer Array Assemblies," Lab Chip, 2012, 12977 (2012).
Kalinina et al. "Nanoliter scale PCR with TaqMan detection", *Nucleic Acids Research*, 1997, vol. 25, No. 10, pp. 1999-2004.
Kim et al. "Protein immobilization techniques for microfluidic assays", Biomicrofluidics, vol. 7, No. 4, 041501, (2013).
Leamon et al. "A Massive parallel PicoTiterPlate based platform for discrete picoliter-scale polymerase chain reactions", *Electrophoresis*, 2003, 24, pp. 3769-3777.
Lindstrom et al., "PCR amplification and genetic analysis in a microwell cell culturing chip", Lab Chip. Dec. 21, 2009; 9(24):3465-71.
Lizardi et al. "Mutation detection and single-molecule counting using isothermal rolling-circle amplification", *Nature Genetics*, vol. 19, Jul. 1998, pp. 225-232.
Malmstadt et al. "A Smart Microfluidic Affinity Chromatography Matrix Composed of Poly(N-isopropylacrylamide)-Coated Beads", Analytical Chemistry, vol. 75, No. 13, Jul. 1, 2003, 2943-2949.
Margulies et al. "Genome sequencing in microfabricated high-density picolitre reactors", *Nature*, vol. 437, No. 15, Sep. 2005, pp. 376-380.
Nagai et al., "Development of A Microchamber Array for Picoliter PCR" Anal. Chem. 2001, 73, 1043-1047 (2001).
Osborne et al. "Single-Molecule Analysis of DNA Immobilized on Microspheres", *Anal. Chem.*, 2000, 72, pp. 3678-3681.
Rissin et al. "Single-molecule enzyme-linked immunosorbent assay detects serum proteins at subfemtomolar concentrations", Nature Biotechnology, vol. 28, No. 6, Jun. 2010.
Rissin et al. "Single-Molecule enzyme-linked immunosorbent assay detects serum proteins at subfemtomolar concentrations", *Nat Biotechnol*. Jun. 2010; 28(6): 595-599.
Rissin, David M. "Single Molecule Detection: Analytical Applications and Fundamental Studies", Dissertation, Tufts University, Apr. 2007, 183 pages.
Schroeder et al. "User Configurable Microfluidic Device for Multiplexed Immunoassays Based on DNA-Directed Assembly", Anal. Chem, 2009, 81:1275-1279.

(56) References Cited

OTHER PUBLICATIONS

Tan et al. "Monitoring the Reactions of Single Enzyme Molecules and Single Metal Ions", *Anal. Chem.*, 1997, 69, pp. 4242-4248.

Zammatteo et al. "Comparison between Microwell and Bead Supports for the Detection of Human Cytomegalovirus Amplicons by Sandwich Hybridization", *Analytical Biochemistry*, 253, 180-189 (1997).

European Office Action for application No. 13794324.7 dated Jan. 25, 2019, 4 pages.

Rissin et al. "Simultaneous Detection of Single Molecules and Singulated Ensembles of Molecules Enables Immunoassays with Broad Dynamic Range" *Analytical Chemistry* 83:2279-2285 (2011).

Rissin et al. "Multiplexed single molecule immunoassays" *Lab on a Chip* 13:2902-2911 (2013).

Chang et al. "Single molecule enzyme-linked immunosorbent assays: Theoretical considerations" *Journal of Immunological Methods* 378:102-115 (2012).

Song et al. "Direct Detection of Bacterial Genomic DNA at Sub-Femtomolar Concentrations Using Single Molecule Arrays" *Analytical Chemistry* 85:1932-1939 (2013).

European Examination Report for application No. 13794324.7 dated Sep. 28, 2017, 6 pages.

Gibbs et al., "Effective Blocking Procedures in ELISA Assays", Corning Incorporated, Life Sciences, Kennebunk, ME USA, 2001-2017, Corning Incorporated, All rights reserved, 10/17, 4 pages.

Michael Steinitz, "Quantitation of the Blocking Effect of Tween 20 and Bovine Serum Albumin in ELISA Microwells", Analytical Biochemistry 282, pp. 232-238 (2000).

Taylor et al., "Impact of surface Chemistry and Blocking Strategies of DNA Microarrays", Nucleic acids Research, 2003, vol. 31, No. 16 e87, 19 pages.

\* cited by examiner

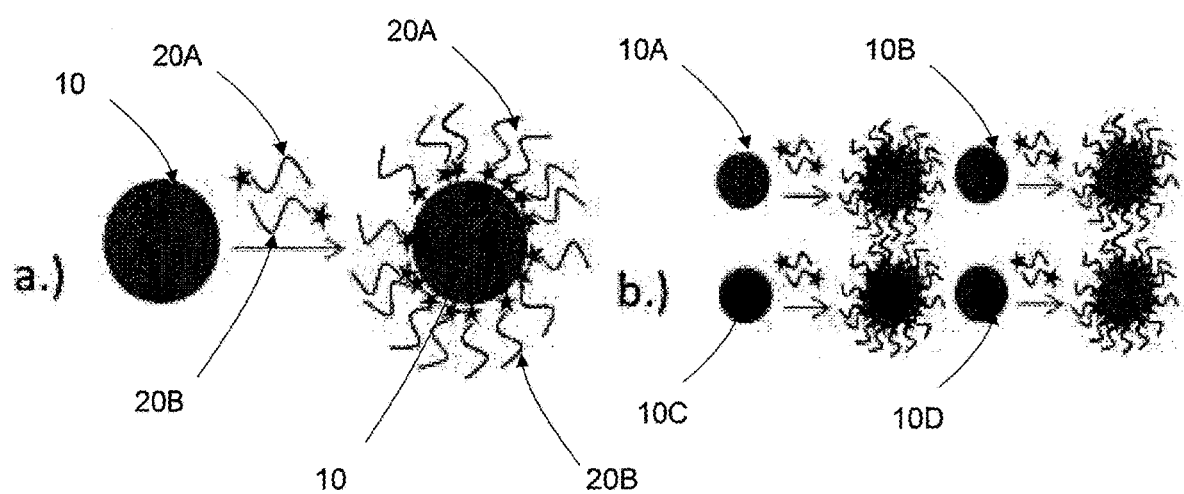
Figure 1A
Figure 1B
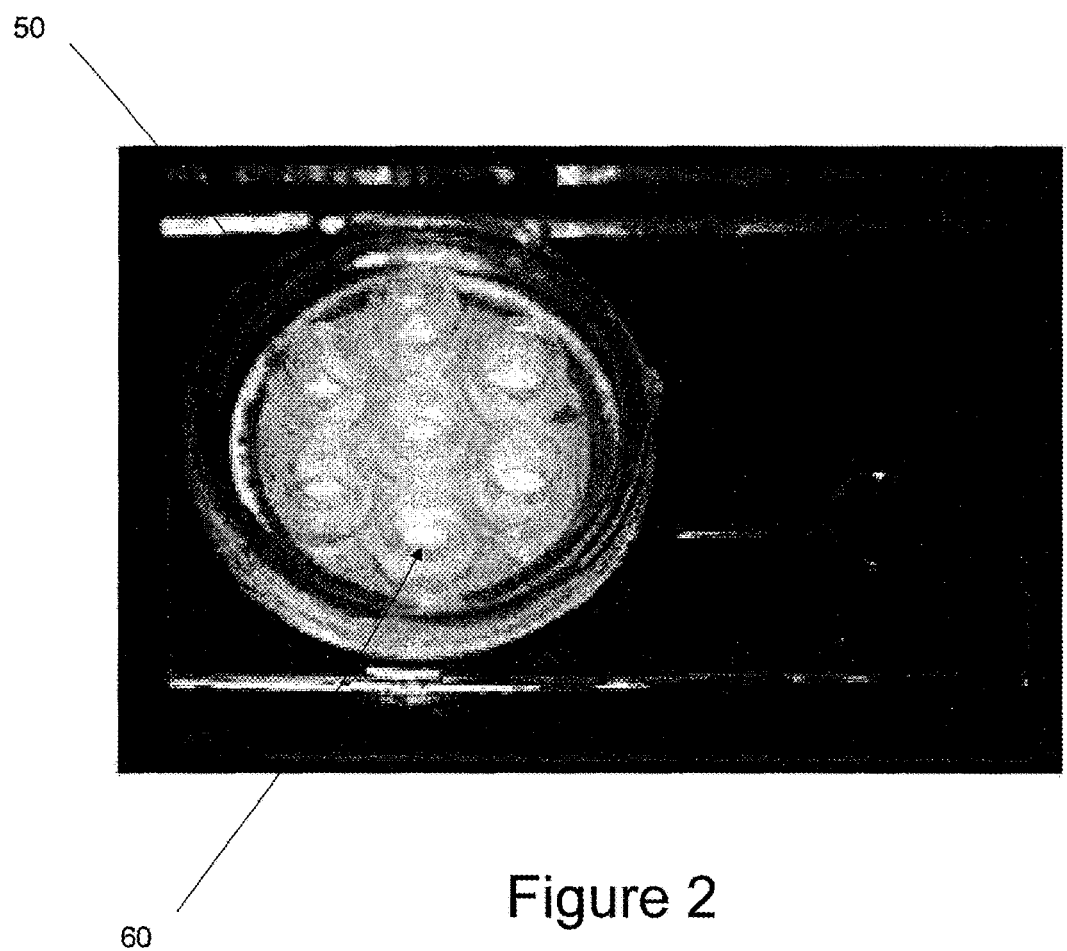
Figure 2

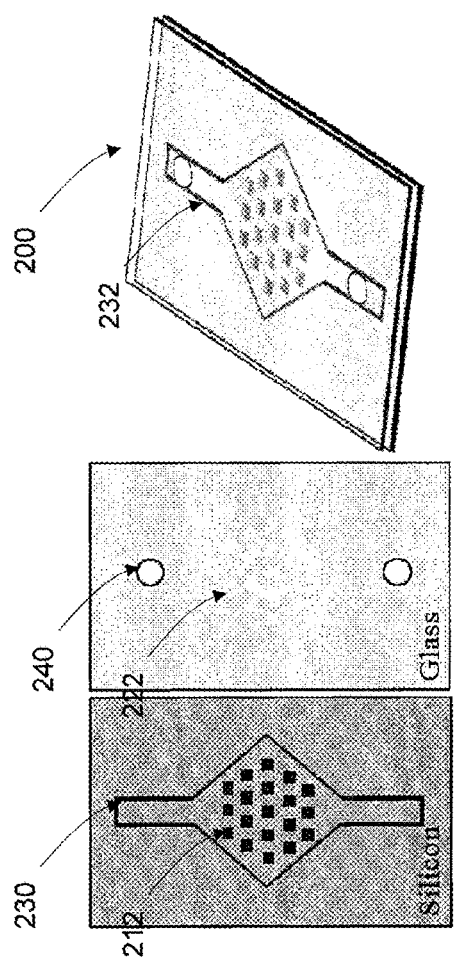
Figure 9
Figure 10
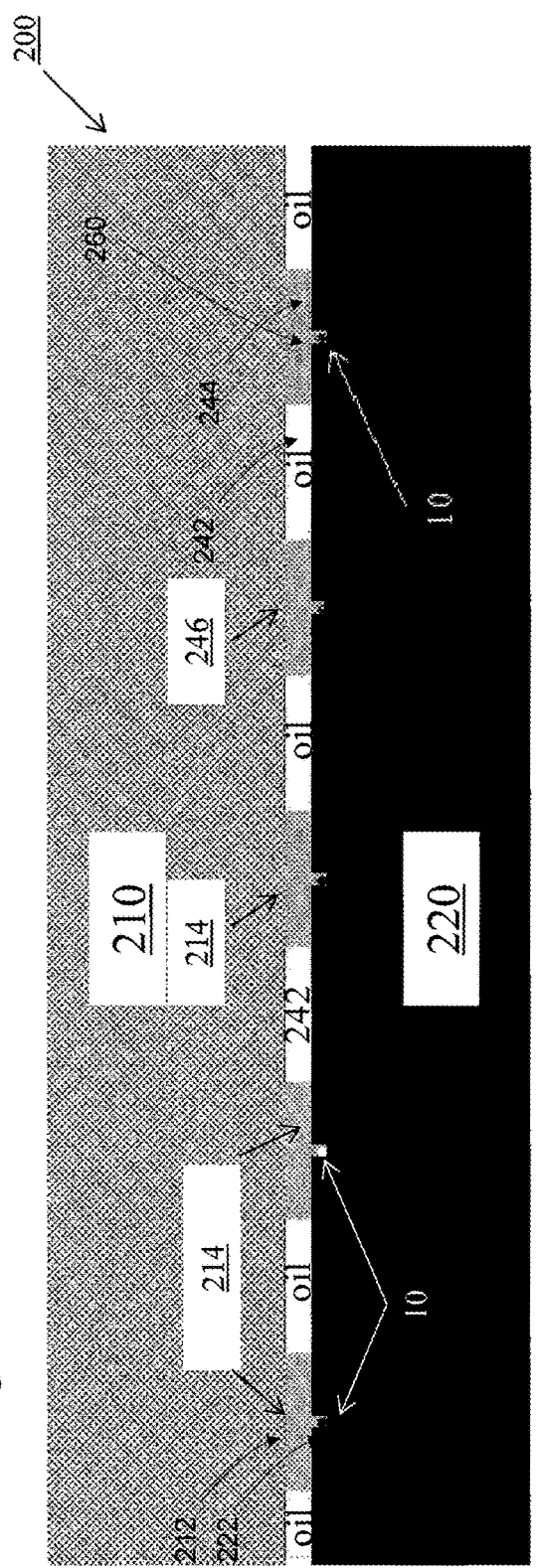
Figure 11

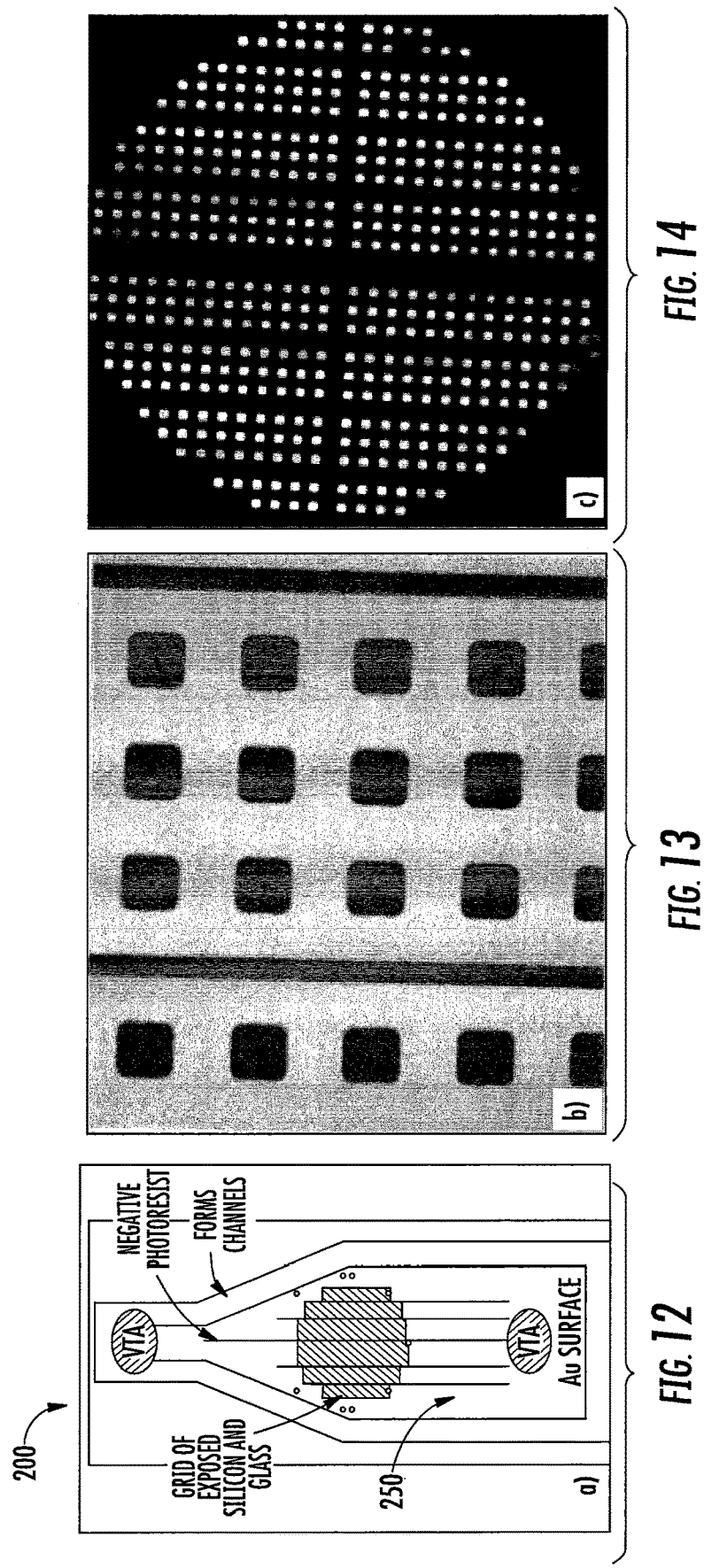

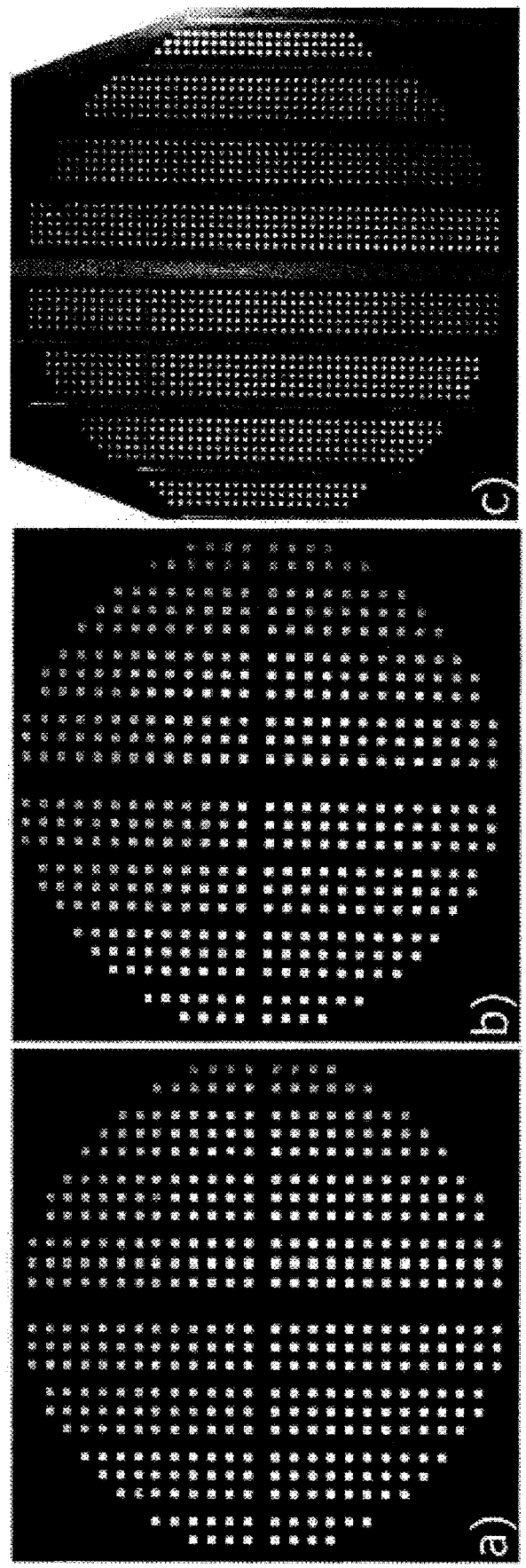

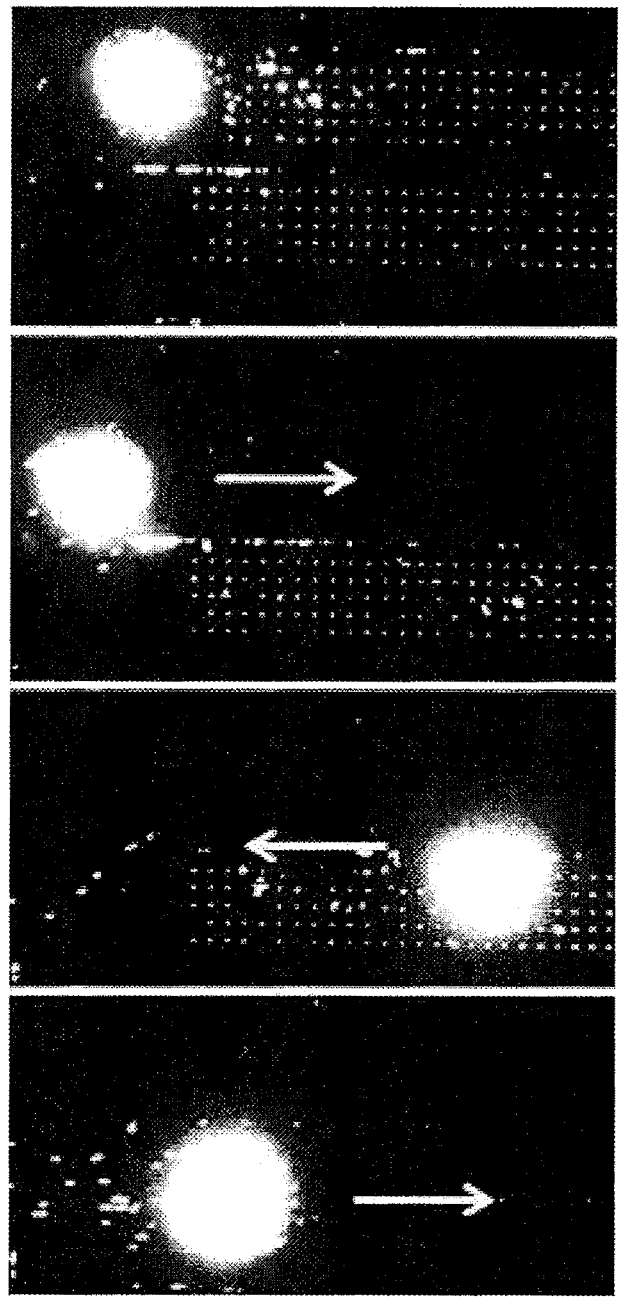

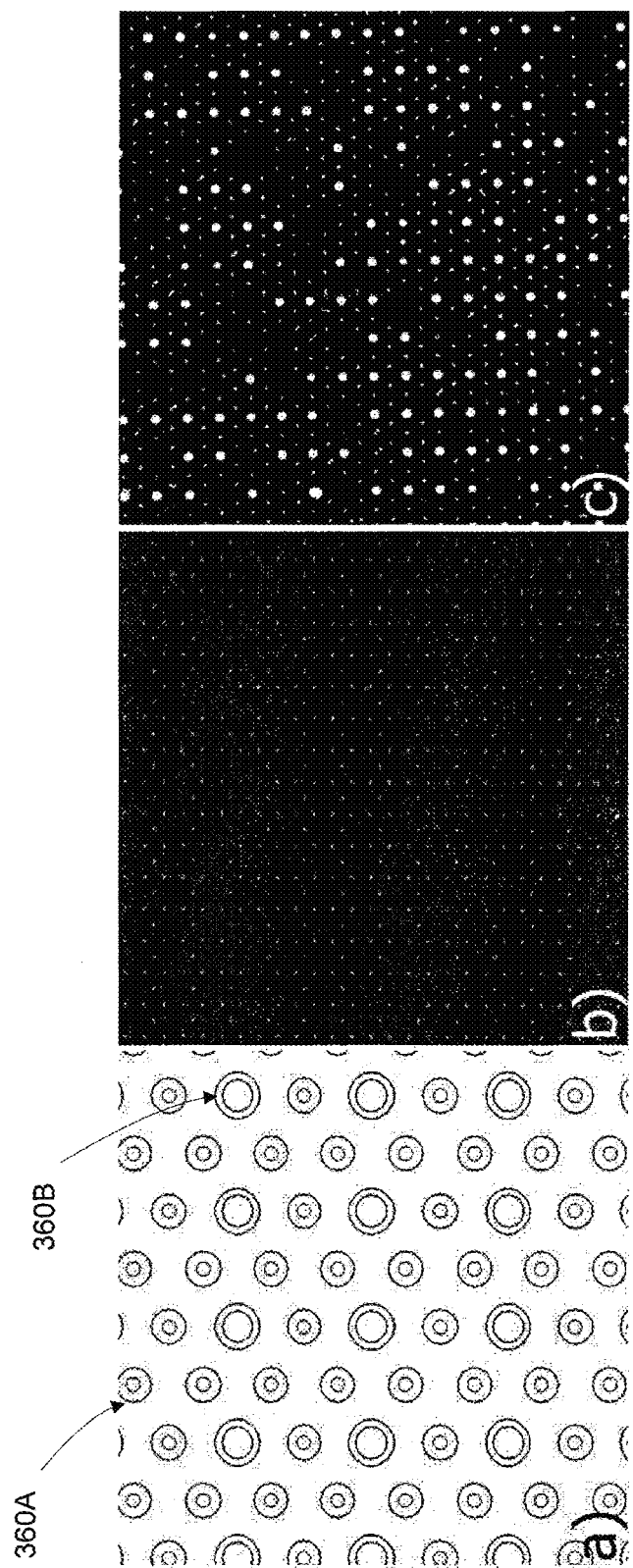

MICROFLUIDIC DEVICES, SOLID SUPPORTS FOR REAGENTS AND RELATED METHODS

RELATED APPLICATIONS

The present application is continuation of U.S. patent application Ser. No. 14/402,565 filed Nov. 20, 2014 which is a 35 U.S.C. § 371 national phase application of PCT International Application No. PCT/US2013/032300, filed Mar. 15, 2013, which claims priority to U.S. Provisional Application Ser. No. 61/651,648, filed May 25, 2012, the disclosures of which are hereby incorporated by reference in their entirety. PCT International Application No. PCT/US2013/032300 is published as PCT Publication No. WO 2013/176767.

FIELD OF THE INVENTION

The present invention relates to microfluidic devices, solid supports for reagents and related methods.

BACKGROUND

The polymerase chain reaction (PCR) is a highly sensitive method for the amplification of segments of genomic DNA (gDNA) or complementary DNA (cDNA). PCR has many applications, for example the detection of trace amounts of nucleic acids to determine the presence of disease causing organisms, gene expression, genotyping, genetic engineering or modification, and forensic science applications. PCR amplification provides outstanding target identification and quantification over a large range of analyte concentrations. However, simultaneous and quantitative analysis of many analytes by PCR has proven to be extremely challenging. Intercalating dye fluorescence-based detection is only capable of determining total dsDNA concentration and therefore concurrent analysis of multiple templates in a single reaction vessel is not possible using this detection method. Fluorescent probe technologies (i.e., Taqman, molecular beacons, or other chemistries) can be used for low-level multiplexing of reactions as each target can be amplified using a different color fluorescence probe as a signaling reporter. Probes are also sequence specific, reducing false positives from primer-dimer formation or nonspecific amplification. A typical method for multiplexing with either conventional microtiter plate or microfluidic real-time-PCR (rt-PCR) is to use a small number of reaction wells, each containing three different color probes. However, it is generally considered challenging to design multiplexed primer and probe sets as they require an additional level of careful design and optimization to insure compatibility with each other. Multiplexing by this method is ultimately limited, by instrumentation and spectral overlap between dyes, to four-color detection, with one color typically reserved for an internal standard dye.

The optimization challenges for multiplexed PCR also create a hurdle to rapid reconfiguration of the assay for emerging diseases or other time-sensitive applications that require analysis of new sequences. Other problems encountered in multiplexed PCR include primer complementarity producing dimers, non-specific interactions between extraneous DNA and amplicons or the primers/probes, and an inherent bias where short sequences are amplified faster than longer ones. Additionally, while using multiplexed reactions divided among a small number of reaction wells can work well for small numbers of targets (~3-12) in systems such as the GeneXpert (Cepheid) or the JBAIDS (Idaho Technology Inc.), this approach becomes cumbersome for significantly larger numbers of targets. Cartridges used with these technologies must be individually loaded with relatively large amounts of liquid reagents either at the point of care or at the point of manufacture. Technology such as the OpenArray Real-Time PCR System from Life Technologies uses preloaded primer/probe sequences dried in an array of approximately 3000 microwells. This technology does not perform sample cleanup or preparation, and it requires multiple, separate pieces of instrumentation to process, load, and analyze samples. Additionally, the preloading of primer/probe sets must be done using printing-based technology that greatly increases the time and expense required for device production.

SUMMARY OF EMBODIMENTS OF THE INVENTION

In some embodiments, a microfluidic device includes a plurality of reaction wells; and a plurality of solid supports. Each of the solid supports has a reagent attached thereto, wherein the reagent is attached to the solid support via a labile reagent/support bond such that the reagent is configured to be cleaved from the support via a cleaving operation.

In some embodiments, the cleaving operation comprises a thermal operation, an addition of a chemical and/or an application of light to the reagent/support bond. The reagent may include a primer for a PCR reaction. The labile reagent/support bond may include a streptavidin-biotin bond and/or avidin-biotin bond. The cleaving operation may include a thermal operation. In some embodiments, the streptavidin-biotin bond is configured to release the reagent from the support when the solid supports are incubated at about 50-99° C. The solid supports may be microbeads, such as magnetic microspheres. In some embodiments, the solid supports comprise a marker. The marker may include a predefined support shape, a predefined support size, a magnetic property and/or optical property of the support. The marker may include a fluorescence marker.

In some embodiments, the plurality of wells and the plurality of solid supports are sized and configured such that only a single one of the plurality of solid supports is received in a corresponding single one of the plurality of wells. The plurality of wells may include a solid support containment region, or a solid support containment region and a reaction region, and the solid support containment region may be configured to receive a single one of the plurality of solid supports. The solid support containment region may have a cross-sectional area that generally corresponds to a size and/or shape of the single one of the plurality of solid supports. In some embodiments, the reaction may occur or be initiated in the solid support containment region which may serve as the reaction region in this case. The reaction region may have a cross-sectional area that is larger than the cross-sectional area of the solid support containment region. The microfluidic device may include a sealing member (elastomeric membrane, such as polydimethylsiloxane) or an immiscible fluid to fluidically isolate each of the plurality of wells. The microfluidic device may include a membrane in the wells. The membrane may be an extraction membrane. In some embodiments, the membrane includes a monolithic aluminum oxide membrane. In some embodiments, a channel is connected to the membrane that is configured to provide a fluid connection to the plurality of wells via the membrane. In some embodiments, the wells are configured to receive a plurality of supports. In some embodiments, a pattern of microposts are between the membrane and the channel to the support the membrane but allow even fluid flow from the plurality of wells via the membrane. In some embodiments, reagents are configured to be released from multiple beads in one of the plurality of wells to effect a reaction between reagents.

In some embodiments, a method for providing a reagent to a microfluidic device comprising a plurality of reaction wells includes providing a plurality of solid supports in the plurality of reaction wells, each of the solid supports having a reagent attached thereto such that the reagent is attached to the solid support via a labile reagent/support bond and the reagent is configured to be cleaved from the support via a cleaving operation. A cleaving operation is performed to release the reagent into a solution in the plurality of reaction wells.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1A is a diagram of a bead having a primer attached thereto according to some embodiments.

FIG. 1B is a diagram of four beads having different encoding properties according to some embodiments.

FIG. 2 is a digital image of a microfluidic device having a plurality of wells for holding the bead/primers of FIGS. 1A-1B.

FIG. 9 is a schematic drawing of a microfluidic device according to some embodiments.

FIG. 10 is a perspective view of the device of FIG. 9 showing alignment of the substrates.

FIG. 11 is a cross-sectional side view of the device of FIG. 9.

FIG. 12 is a top view of a schematic diagram showing a microfluidic device having photoresist lanes to control fluid flow according to some embodiments.

FIG. 13 is an optical microscopy image of the device of FIG. 12 showing 100 µm by 100 µm pads where a gold layer was removed. Bead wells are located in the center of the wells.

FIG. 14 is a fluorescence image of a dye solution isolated on 444 pads in the device of FIG. 12. No bridging and few stray droplets are seen.

FIGS. 15A-15B are fluorescence images of microfluidic devices according to some embodiments with 440 hydrophilic reaction region (100 µm×100 µm wells) that isolate 250 pL using a photoresist spacer 25 µm tall (FIG. 15A) and 75 pL using a 7.5 µm spacer (FIG. 15B).

FIG. 15C is a fluorescence image of a microfluidic device according to some embodiments including 1500 reaction regions (50 µm×50 µm wells) with a 9 µm spacer to isolate 22.5 pL volumes.

FIGS. 18A-18D is a series of fluorescence images showing the magnetic loading of beads according to some embodiments. A clump of more than 15,000 beads may be seen as a large mass in each frame, and arrows indicate the direction in which the clump of beads is being drawn by the magnet under the device.

FIG. 19A identifies Qdot 605 and primers for the mecA gene (365/10 nm ex); FIG. 19B identifies Qdot 655 and primers for S. mutans; and FIG. 19C identifies beads without Qdot labels that carry primers for the nuc gene found in S. aureus gDNA. Both Qdot 605 and Qdot 655 labeled beads fluoresce brightly. An empty bead well is shown in FIG. 19C that is highlighted with a white hexagon.

FIG. 22A is a schematic image of a microfluidic device according to some embodiments in which different well sizes preferentially retain correspondingly sized beads according to some embodiments.

FIGS. 22B-22C are fluorescence microscopy images illustrating the bead acceptance patterns of the device of FIG. 22A.

DETAILED DESCRIPTION OF EMBODIMENTS OF THE INVENTION

Figure 3:
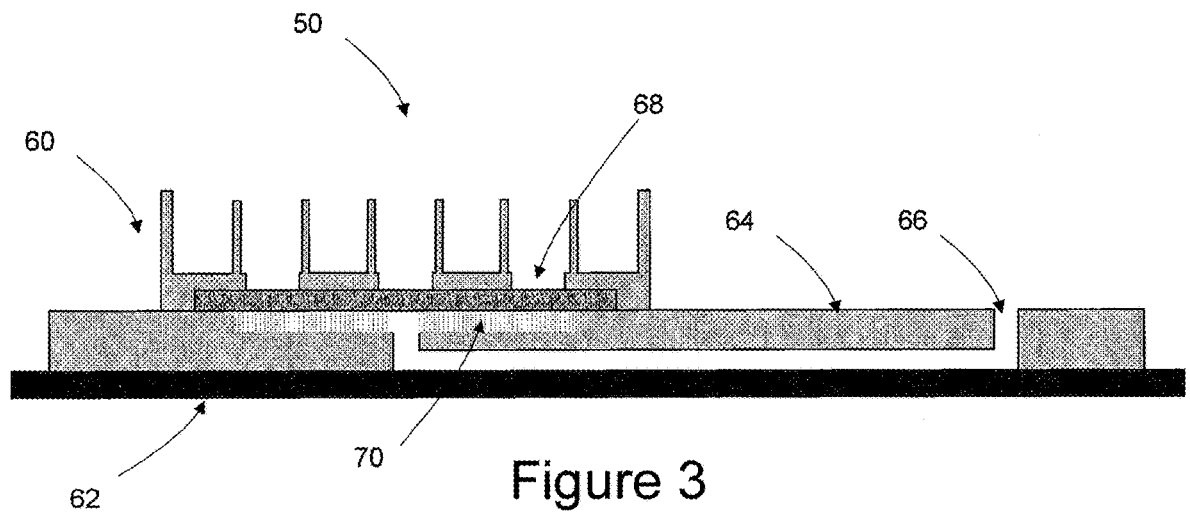
FIG. 3 is a cross-sectional side view of the microfluidic device of FIG. 2.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., or any combination thereof as are well known in the art.

Probes and primers, including those for either amplification and/or detection, are oligonucleotides (including naturally occurring oligonucleotides such as DNA and synthetic and/or modified oligonucleotides) of any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well, and/or coupled to or labeled with a detectable group such as a fluorescent compound, a chemiluminescent compound, a radioactive element, or an enzyme.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. The amplified sequence can also be detected by adding an intercalating dye to the reaction mixture and monitoring the fluorescence signal strength, which will be proportional to the total mass of double stranded DNA. Although embodiments according to the present invention are described with respect to PCR reactions, it should be understood that other nucleic acid amplification methods can be used, such as reverse transcription PCR (RT-PCR) including isothermal amplification techniques such as rolling circle amplification or loop-mediated isothermal amplification (LAMP).

DNA amplification techniques such as the foregoing can involve the use of a probe, a pair of probes, or two pairs of probes which specifically bind to DNA containing a polymorphism or mutation of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

The term "reagent" refers to any substance or compound, including primers, the nucleic acid template and the amplification enzyme, that is added to a system in order to bring about a chemical reaction, or added to see if a reaction occurs. Amplification reagents or reagent refer to those reagents (deoxyribonucleotide triphosphates, buffer, etc.) generally used for amplification except for primers, nucleic acid template and the amplification enzyme. Typically, amplification reagents along with other reaction components are placed and contained in a reaction vessel (test tube, microwell, etc.).

The term "magnetic" as used herein includes ferromagnetic, paramagnetic and super paramagnetic properties.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below. Such probes are sometimes referred to as detection probes or primers herein.

Kits useful for carrying out the methods of the present invention will, in general, comprise one or more solid supports having reagents attached thereto and other reagents for carrying out the methods as described above, such as restriction enzymes, optionally packaged with suitable instructions for carrying out the methods. The kits may also include containers for housing elements included therein. Such containers include, but are not limited to, vials, ampoules, tubes, capsules, bottles, syringes, bags, microfluidic chips and cartridges, including preloaded bead devices.

As illustrated in FIG. 1A, a solid support or bead 10 may have primers 20A, 20B attached thereto. The primers 20A, 20B may be a pair of biotinylated primers, and the bead 10 may be streptavidin-labeled such that binding of the biotinylated primers to the beads occurs. In some embodiments, the beads 10 may include a marker, such as an optical marker, that may be used during analysis to identify the primers 20A, 20B anchored to the respective beads 10A. For example, as shown in FIG. 1B, different encoded beads 10A, 10B, 10C, 10D may be marked for identification of different attached primer sets during analysis. Various pre-encoding methods may be used to provide a marker on the bead 10 or other solid support, including a predefined size, shape, magnetic property and/or fluorescence doping used alone or in combination with other encoding methods. Both custom-sequence biotinylated primers and streptavidin labeled paramagnetic magnetic beads can be readily purchased from commercial vendors or made in a suitable quantity in an appropriately equipped laboratory.

Although embodiments according to the present invention are described herein with respect to beads 10 (e.g., magnetic microspheres) it should be understood that any suitable solid support may be used, whether porous, superficially porous, or nonporous. Supports may include, but are not limited to magnetic or non-magnetic particles or granules made of materials such as polymer or plastics, glass, silicon dioxide or metal or semimetal oxides (including but not limited to aluminum oxides, titanium oxides, zirconium oxides or other oxides), quantum dots, photolithographically fabricated particles or structures (discrete or nondiscrete), filter membranes or elements, solid surfaces of vials, microtiter plates, microfluidic or macrofluidic reaction wells, silicone or other rubbers, metals and metal particles, naturally occurring supports or absorbents suited for these purposes.

Although embodiments according to the present invention are also described herein with respect to PCR reactions, it should be understood that the microfluidic devices, beads and reaction methods described herein may be used in various other reactions, e.g., where reagents are cleaved from a bead into a well to participate in a reaction. For example, any nucleic acid transcription and/or amplification-related reaction is within the scope of the current invention, including but not limited to PCR reactions, real-time PCR (rt-PCR), digital PCR (dPCR), reverse transcription of RNA into cDNA (RT), PCR of cDNA from previous RT step (RT-PCR), RT-PCR using real-time or digital quantification, immuno-PCR (iPCR) and its variants, loop-mediated isothermal amplification (LAMP), rolling circle replication, and/or non-enzymatic nucleic acid amplification methods (e.g., "DNA circuits"). Other reactions that are included within the scope of the present invention include but are not limited to enzyme-linked immunosorbent assays (ELISA) where the fluorogenic substrate is bound to the support surface to be cleaved at some point for subsequent reaction, single molecule array (SiMoA) or digital ELISAs where the fluorogenic substrate is bound to the support surface to be cleaved at some point for subsequent reaction, reactions in which multiple beads are used to deliver different reagents for combinatorial chemistry, reactions where the beads deliver a catalyst reagent, and/or reactions where "click" chemistry reagents are delivered in stoichiometries determined by stochastic bead loading.

Any suitable coupling chemistry may be used to bind the primers 20A, 20B to the beads 10. In some embodiments, the primers 20A, 20B may be attached to the beads 10 using labile chemical bonds, such as bonds that may be cleaved using various techniques. For example, thermal energy may be applied to break or cleave a chemical bond or light may be applied to break a photo-cleavable bond. Thermal heating may be accomplished by conductive contact with a hot surface, Joule heating of a solution, resistive heating of a substrate that is adjacent the beads 10, exposure to electromagnetic radiation and/or electromagnetic induction. In some embodiments, the chemical bonds may be cleaved using ionizing radiation, a chemical agent, an enzyme, an electrochemical process, a change in pH, or other suitable cleaving operations. For example, a change in pH may be caused by electrochemical reactions occurring at the surface of the region holding the beads 10 or a change in conditions may be directly or indirectly caused by an activation of an initiator reagent, which itself may be activated by a physical changes such as heat, light, electrochemical processes, change in pH, etc. The primers 20A, 20B may be anchored to the bead 10 such that the primers may remain anchored during storage, sample preparation and/or the washing steps before the PCR. A cleaving operation may be performed when the PCR reaction takes place to disengage the primers 20A, 20B from the beads 10. Depending on the particular labile chemical bond used, the cleaving operation may include the application of heat, light and/or addition of a chemical to disengage the primers 20A, 20B from the beads 10. When the primers 20A, 20B are disengaged from the beads 10, the primers may readily participate in the PCR reactions, and when the primers 20A, 20B are anchored to the beads 10, the primers 20A, 20B generally do not react in the PCR reaction unless template DNA is in close proximity. Although embodiments according to the present invention are described with respect to the primers 20A, 20B, it should be understood that the any suitable reagent may be used as elements 20A, 20B and bound with any suitable chemical bond. For example, any reagent, probe or oligonucleotide may be used. Suitable cleavable bonds in addition to streptavidin-biotin include, but are not limited to photo-cleavable biotin, avidin, streptavidin, and captavidin, and may be commercially available, for example, from Ambergen (PC Biotin Phosphoramidite, PC Amino-Modifier Phosphoramidite and PC Spacer Phosphoramidite).

As illustrated in FIGS. 2-3, a microfluidic device 50 may include a plurality of wells 60. The beads 10 and primers 20A, 20B attached thereto may be pre-loaded into the wells 60. The device 50 may further include a substrate 62 (e.g., glass) and a microfluidic portion 64 having a channel 66 for fluidically connecting to the wells 60. As illustrated in FIG. 3, the wells 60 may be formed on a membrane 68, such as a monolithic aluminum oxide membrane (AOM). The membrane 68 may be used to purify DNA from a sample. Other suitable materials for sample cleanup may be employed including polymer membranes or inorganic or polymer surfaces that can perform a solid phase extraction or another method of separation. The membrane can be supported on a patterned grid or array of microposts 70 connected to a channel such that the membrane is fully supported but fluid may still flow through it freely and evenly. Accordingly, the primers 20A, 20B on the beads 10 may be preloaded into the wells 60 and stored for a period of time before use. The wells 60 may each contain beads 10 having many copies of a single primer pair and be labeled for ease of analysis.

Figure 4:
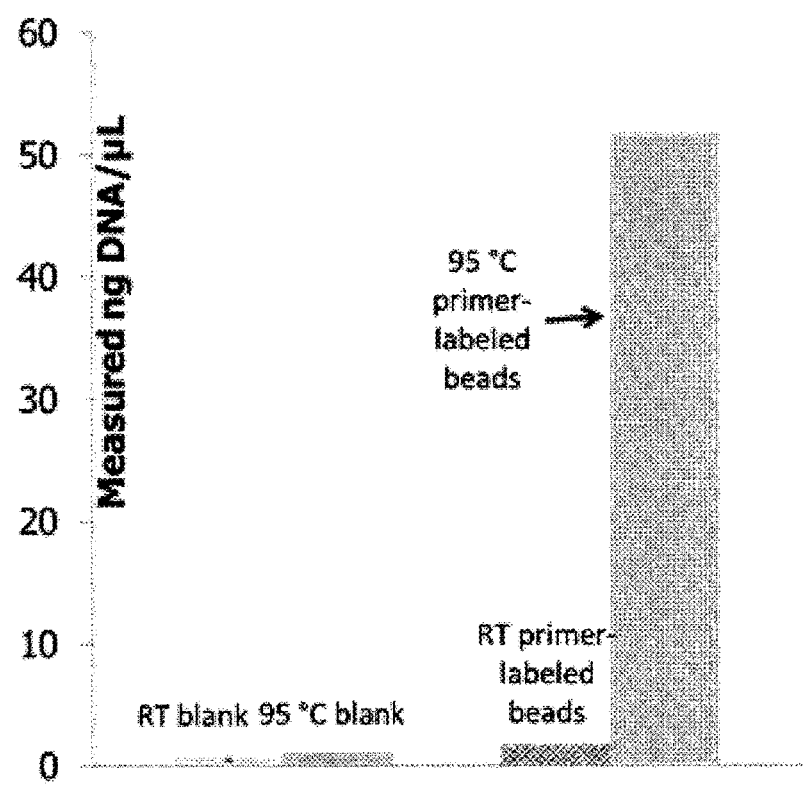
FIG. 4 is a bar graph showing a measured amount of DNA (ng/µL) and indicating an amount of primer released from the beads at room temperature and at 95° C. and for a sample without primer beads.

In some embodiments, the primers 20A, 20B are attached to the beads 10 via a streptavidin-biotin bond. The streptavidin-biotin bond is one of the strongest known non-covalent bonds found in biological systems, but it is heat labile. When biotinylated primers are reacted with streptavidin-coated microspheres before PCR, the primers are significantly captured onto the surface of the beads. Washing or other sample processing steps in a suitable buffer can be conducted without generally releasing the primers. However, upon heating the beads 10 or otherwise denaturing the streptavidin, large amounts of primers are released from the surface and can participate in PCR reactions. FIG. 4 is a graph of measurements using a NanoDrop 2000 UV-Vis absorbance detector of the supernatant liquid from a suspension of beads labeled in this manner with primers specific for a region of *Staphylococcus aureus* target DNA. As illustrated, at a range of temperatures from room temperature (RT) to <50° C., there is no detectable release of primers, even after several days' storage at 4° C. or when stored dry at room temperature in the wells of the microfluidic device for more than 2 months. When incubated at 95° C., primers are released and can be readily detected in the supernatant.

High levels of bead functionalization with all biotinylated primer sets tested to date have been observed. The attachment is stable for more than 60 days when stored dry at room temperature, and beads stored in solution at 4° C. for >11 months have been tested and activity in PCR reactions was still observed.

Figure 5A:
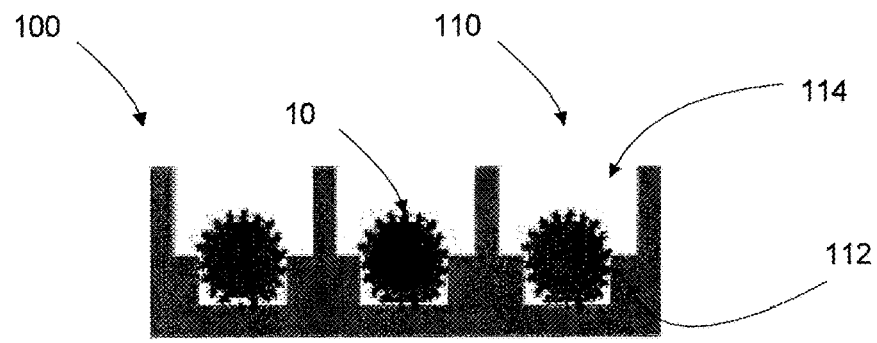
FIGS. 5A-5D are diagrams illustrating a microfluidic device configured to receive individual beads in respective wells according to some embodiments.
Figure 5B:
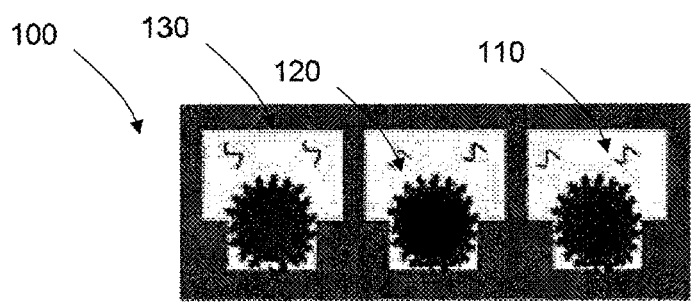
Figure 5C:
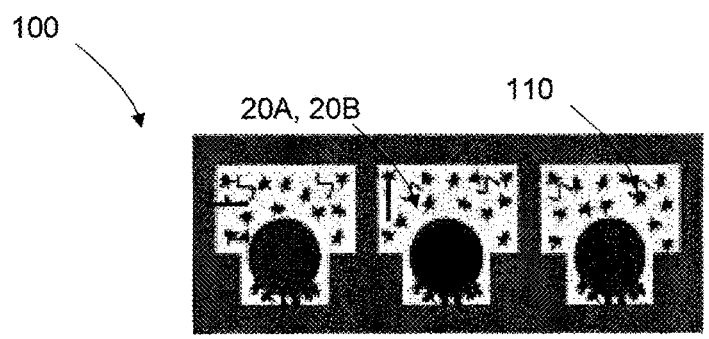
Figure 5D:
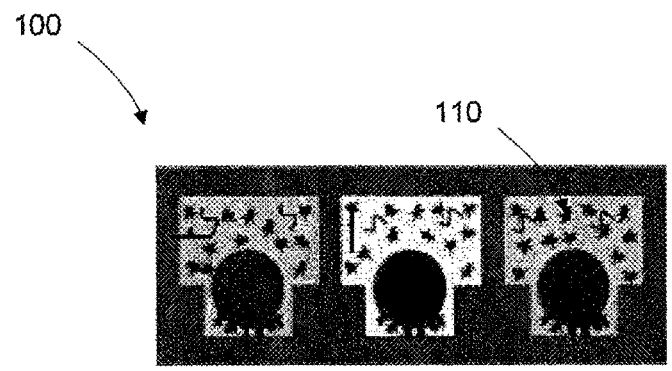

In some embodiments, a bead set may be labeled with various primers for a PCR reaction (e.g., forward and reverse primers, and/or hybridization probe) as illustrated in FIG. 1B. The beads 10 may be decoded by dyes, size, shape, magnetic properties, or other detectable and/or optical physical properties or a combination of properties such that each bead set with predefined primer pairs may be distinguished from one another. As illustrated in FIG. 5A, a microreaction well array 100 may be provided that includes a plurality of wells 110. Each well 110 includes a support or bead containment region 112 and a reaction region 114. Dimensions of the beads and the wells should be proportional such that the appropriate amount of reagent (primers, probes, etc.) is delivered. The bead containment region 112, if used, may be similarly sized to the bead diameter. The reaction region 114 can range from submicron to millimeter dimensions with volumes ranging from subfemtoliter to hundreds of microliters. The bead containment regions 112 and the bead 10 can range from submicron to millimeter size as appropriate for the desired reaction. The bead containment region 112 is sized and configured to contain a single bead 10. Therefore, the beads 10 may be loaded into the individual reaction wells 110 separately. As shown in FIG. 5B, a reaction solution 120 is added to the wells 110 and the wells may be sealed with a cover 130 or other sealing member such as an immiscible fluid or oil such that the reaction wells 110 are fluidically isolated from one another. As shown in FIG. 5C, a cleaving operation can be performed to separate the primers 20A, 20B from the beads 10. For example, the device 100 may be heated to release the primers 20A, 20B from a streptavidin-biotin bond. However, depending on the type of bond between the primers 20A, 20B and the bead 10, other cleaving operations may be used, including the application of light or chemicals. As illustrated in FIG. 5D, the bead encoding and PCR reaction results may be read to determine 1) the type of bead 10 in the wells 110 (and the corresponding primers in the reaction in the well 110), and 2) the presence and/or concentration of each respective template molecule being detected. For example, if fluorescence encoding of a particular wavelength is used on the beads 10 to identify the relevant primer 20A, 20B, then the fluorescence encoding signal is read at that wavelength before, during, or at the end of PCR. The signal from the intercalating dye or probe used to determine the concentration or presence of amplicon can be read at another wavelength. This signal along with the encoding information may then be used to determine the presence and/or concentration of each template molecule.

Accordingly, in this configuration, the beads 10 may be stochastically distributed in the microwells 110 without a complicated deterministic loading or printing technique. The primer set and/or probe of each of the beads 10 in the microwells 110 may be determined after the beads 10 are loaded and/or after the reaction is performed. Therefore, relatively large numbers of very small reaction wells 110 that can be loaded stochastically from a mixture of all the desired bead sets may be used. The device 100 may use a set of microwells 110 patterned into a substrate that mates to a sealing member or cover 130 or an overlay of immiscible fluidic such as oil, liquid polymer, or fluorocarbon liquid that will seal in a manner where each well 110 is fluidically isolated from its neighbors such that each PCR reaction is fully isolated. In some embodiments, the device 100 (having a substrate and wells) and the cover 130 may be made from a combination of one rigid and one deformable elastomeric material so that a sufficient seal can be made by the application of pressure to the external surfaces of the device 100. The use of pre-encoding methods (size, fluorescence doping, shape, magnetic properties, among others, used alone or in combination) may be implemented for very small reaction volumes (e. g., between about 1 cL to 1 µL or less than about 1 µL) where only a single bead 10 is needed to provide the necessary primers or other specific reagent(s). In this case, beads 10 may be loaded into microreaction wells 110 such that each well 110 contains only one bead 10 and sufficient volume for the PCR reaction to take place. In some cases, the volume of the bead well that is not displaced by the bead may be sufficient volume for a reaction to occur. In this case, the bead well can serve to both hold the bead as well as to define the reaction volume. The different sets of primer-labeled and/or probe-labeled beads 10 can be mixed together into a single solution. The identity of the primer set (or other reagent) can then be determined from the encoding of the beads 10. Sampling may be conducted either by simple inclusion within the well 110 (generally at high concentrations of template) or by direct hybridization to the primer sets or other affinity reagents (including but not limited to antibodies or aptamers) bonded to the bead 10 (generally at lower concentrations of template). In some embodiments, hundreds to billions of parallel, singleplex quantitative PCR reactions may be performed within a single, small-footprint device 100.

As shown in FIGS. 9-11, a microfluidic device 200 includes two substrates 210, 220 that are separated by a channel-forming photoresist or other spacer 230. The height of the spacer 230 defines a gap between the substrates 210, 220 and a channel 232. The substrates 210, 220 include respective hydrophobic regions 212, 222 and hydrophilic regions 214, 224 that spatially correspond to one another such that when the substrates 210, 220 are in an assembled configuration (FIG. 10), the hydrophobic regions 212, 222 and hydrophilic regions 214, 224 align with one another. One of the substrates 210 includes apertures 240 that fluidically connect to the channel 232. One of the substrates 220 further includes etched bead wells 260.

In this configuration, beads 10 as described herein may be positioned in the bead wells 260. A non-aqueous fluid 242 and an aqueous solution 244 may be positioned in the channel 232 to form reaction regions 246 of generally isolated aqueous solution 244 that is in fluid contact with a respective one of the beads 10.

In some embodiments, the beads 10, the non-aqueous solution 242 and the aqueous solution 244 may be loaded into the device 200 as follows. A plurality of beads 10 may be inserted into the apertures 240 and loaded into the wells 260. For example, the beads 10 may be magnetic beads, and a magnet applied to an exterior of one of the substrates 210, 220 may be used to drag the beads 10 across the channel 232 such that the beads 10 fall into the wells 260 and remain in place. The wells 260 may be sized and configured to accommodate a single bead 10. A buffer may be flushed through the channel 232 to remove any excess beads 10 that were not loaded into the wells 260. An aqueous fluid may then be added to the apertures 240 followed by a non-aqueous fluid. The aqueous fluid may form reaction regions 246 adjacent the hydrophilic regions 214, 224 that are separated by the non-aqueous fluid 242.

Although the microfluidic device 200 is described above with respect to wells 260 and the reaction region 246 in the hydrophilic regions 214, 224, it should be understood that the reaction region 246 and wells 260 may instead be positioned in a hydrophobic region such that the reaction occurs in a non-aqueous fluid depending on the reaction environment desired. In some embodiments, the aqueous fluid is a fluid including the components of a desired reaction, such as a PCR master mix. The substrates 210, 220 may be formed of any suitable material, such as plastic, glass, or silicon or combinations thereof. Lipophobic patterning can also be used, for example a fluorocarbon-based coating with a fluorocarbon-based oil phase.

The hydrophilic regions 214, 224 and hydrophobic regions 212, 214 may be formed by depositing a hydrophilic or hydrophobic layer on the substrates 210, 220 and may or may not require subsequently removing part of the layer, depending on the hydrophilic or hydrophobic properties of the substrates 210, 220. For example, gold may be deposited on a hydrophilic substrate, such as silicon or glass, and then etched to form hydrophilic regions of the substrate and hydrophobic regions of gold. Alternatively, patterning may be done by selective modification of the existing surface, such as plasma treatment of regions of native surfaces of plastic substrates.

As described above, the beads 10 may be loaded into the wells 260 randomly, and a subsequent operation may be used to determine which bead type corresponds to specific locations on the device 200. For example, if the beads 10 include an optical marker that is associated with the particular primer or other reagent attached to the beads 10, then an optical imager, such as a microscope, may be used to optically identify which primer is associated with a given well location for subsequent analysis.

In some embodiments, the wells 260 may be sized and configured to preferentially retain a particular bead type based on a size and/or shape so that, for example, larger beads would be retained by larger wells and smaller beads would be retained by smaller wells. For example, as illustrated in FIG. 22A, a schematic of a silicone chip design with 2.1 µm bead wells 360A and 5.6 µm bead wells 360B to hold 3 and 6 µm diameter beads, respectively, is shown. In this chip design, the smaller silicone wells expand to accept a slightly larger diameter bead, but smaller beads will not be retained in larger diameter bead wells. The outer outlines indicate reaction well geometry around each bead well. FIG. 22B is a fluorescence microscopy image showing chip loaded with only 3 µm beads. FIG. 22C is an image showing the chip loaded with a mixture of 3 and 6 µm beads and illustrates the ability to preferentially load beads into particular wells based on size encoding.

Moreover, in some embodiments, nonspecific, "parasitic" reactions may be substantially reduced by the isolation of the reaction into multiple, smaller volumes using the solid supports in solid reaction wells, e.g., to reduce primer dimers. Segmentation of the reaction into multiple smaller reactions using these principles is applicable to many different reactions. By multiplexing using the beads 10 according to some embodiments, the formation of an emulsion (such as used with emulsion PCR) is not generally required to accomplish reaction segmentation. Emulsions may increase the complexity and/or cost of preparation, limit the range of reaction volumes and require chemical species with a propensity to form emulsions).

In addition, it should be understood that some or all of the processes described herein may be automated, e.g., using pumps, valves, optical imaging devices, and the like.

Embodiments according to the present invention will now be described with respect to the following non-limiting examples.

Example 1

Figure 6:
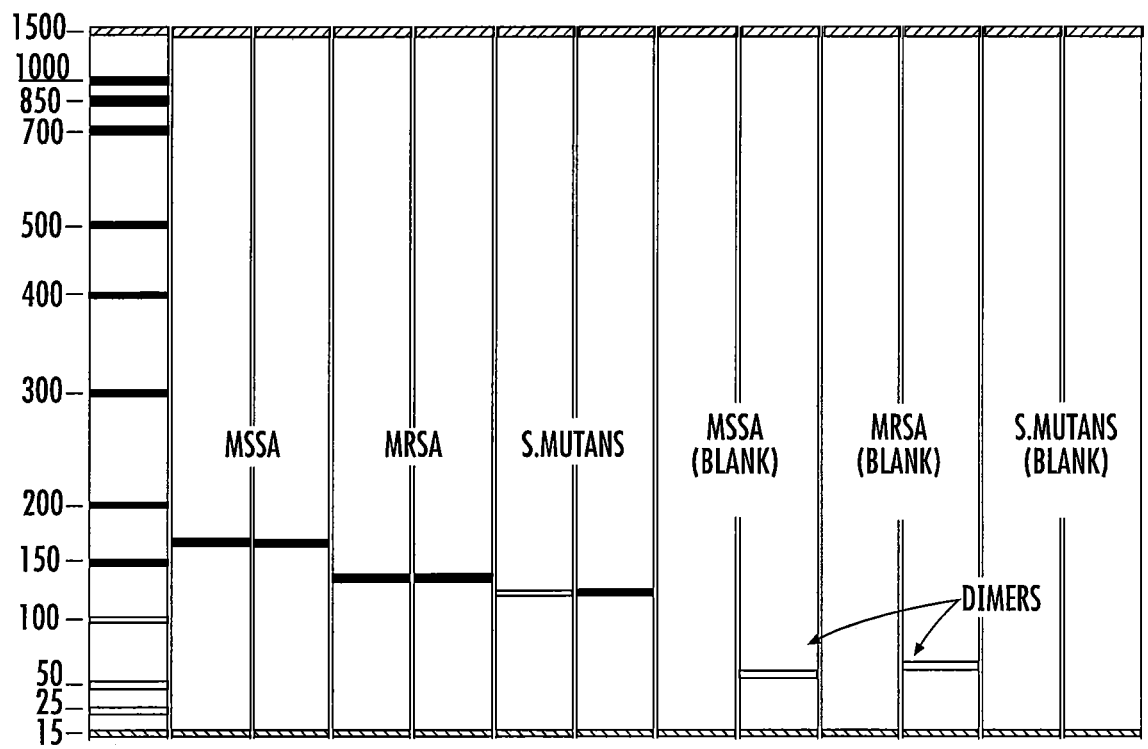
FIG. 6 is a plot of data showing PCR amplification of three different template sequences using three different bead sets according to some embodiments.

PCR was performed in standard 200 µL PCR-grade polypropylene tubes with a total reaction volume of 10 µL with sets of beads containing biotinylated primer sequences for *S. aureus*, the mecA gene found in Methicillin-resistant *S. aureus* (MRSA), and *Streptococcus mutans* purchased from IDT (Coralville, Iowa) and bonded to streptavidin-coated beads (Bangs Laboratories, Inc., product #PMS3N/10098). Two different concentrations of beads were used, one containing 2.5 µg of beads (~60 nM equivalent primer concentration) and one containing 5 µg of beads (~120 nM primer concentration). Approximately 300-400 copies of purified gDNA from each species were added to the corresponding reaction tubes. The PCR master mix containing all the reagents needed for PCR except primers was added and the tubes were thermocycled for 50 cycles. FIG. 6 shows the subsequent analysis performed on the supernatant using an Agilent Bioanalyzer 2100 using the DNA1000 kit. The first lane for each analyte shows the results for PCR reactions that contained 2.5 µg of beads, and the second lane shows result from reactions that contained 5 µg of beads. Blanks were also run for each bead concentration. Primer dimers (typically indicative of high primer concentrations) are evident for the Methicillin-susceptible *S. aureus* (MSSA) and MRSA blank reactions. Reducing the amount of beads to 2.5 µg eliminated dimer formation for these reactions. Strong amplicon bands were seen for tubes containing template DNA for MSSA and MRSA at the 2.5 µg bead concentration and *S. mutans* at the 5-µg bead concentration. Dimers were not significant at either bead concentration in samples that contained template DNA. These results demonstrate how primers can be attached to beads, delivered to reaction wells, and then participate in specific PCR amplification reactions after a cleaving operation.

The device 50 of FIGS. 2-3 was used to place beads into specific wells 60 (i.e., deterministic loading) in a known pattern. In contrast to multiplexed reactions in a single well, each reaction is singleplex, so an intercalating dye can be used for detection, reducing the optimization time greatly as compared to traditional multiplex PCR that requires multiple primer/probe sets with different fluorophores. Reconfiguration or incorporation of new bead sets for different assays may be accomplished simply by replacing the bead sets or adding more reaction wells to the chip or device 50.

Transfer of liquids onto the device 50 was conducted by hand; however, it should be understood that liquid handling could be easily automated. Pre-labeled beads with unique primers may be loaded into individual wells 60 using simple reagent dispensing technologies. The solution is allowed to dry, leaving the beads on the surface of the AOM 68 (or other solid phase extraction surface or material).

The sample can be pretreated by heat, reagent addition, centrifugation, enzymatic digestion, or other methods. The sample is dispensed into each well 60 that already contains preloaded primer beads and a vacuum is applied at the waste reservoir or channel 66 to pull the sample fluid through the AOM 68 to capture the analyte on the AOM. Wash buffer(s) can then be dispensed into the reaction wells 60 and removed by vacuum applied at the channel 66 if desired. As the primers are anchored to the beads, they will not be washed away during these sample clean up steps. After sample cleanup, a PCR master mix containing all reagents needed for PCR except primers is added to all the reaction wells 60 and the device 50 is thermocycled. As the master mix contains no template-specific primers, the same master mix can be used in all reactions. The elevated temperatures used for denaturation of DNA during PCR also denature the streptavidin, causing the subsequent release of the biotinylated primers during the first rt-PCR cycle thereby initiating amplification of target DNA. The released primers freely interact with target DNA in the reaction well whether or not it was directly hybridized to the primers on the beads before PCR was initiated. Coupling chemistries other than streptavidin-biotin can be used in some embodiments, including attachment of primers to beads using chemical bonds that can be cleaved using heat, a chemically induced change, or a photo-induced change of the bonds. Since the primers are released freely into the solution contained within the reaction well 60, non-hybridized DNA and double stranded DNA (dsDNA) that is trapped by the solid phase extraction membrane 68 (such as an AOM) is easily detected. Therefore, rapid sample clean up can be performed on both single stranded (ssDNA) and dsDNA without a denaturation step that is normally required to convert dsDNA to ssDNA before hybridizing the sample DNA directly oligomers bound to beads. Since the primers are attached to the beads, in some embodiments, DNA can be extracted with the AOM without washing them away, then the release of the primers into solution allows PCR for amplifying/detecting the extracted DNA. The AOM may permit rapid sample cleanup. DNA extraction could also be performed through hybridization of the target ssDNA to the primers coupled to the beads or adsorption of target DNA to the bead surfaces.

Although the above example is discussed with respect to PCR reactions, it should be understood that similar procedures may be used for any suitable reaction, such as any nucleic acid transcription and/or amplification-related reaction, enzyme-linked immunosorbent assays (ELISA) where the fluorogenic substrate is also bound to the support surface, single molecule array (SiMoA) where the fluorogenic substrate is also bound to the support surface, reactions in which multiple beads are used to deliver different reagents for combinatorial chemistry, reactions where the beads deliver a catalyst reagent, and/or reactions where "click" chemistry reagents are delivered in stoichiometries determined by stochastic bead loading.

Figure 7:
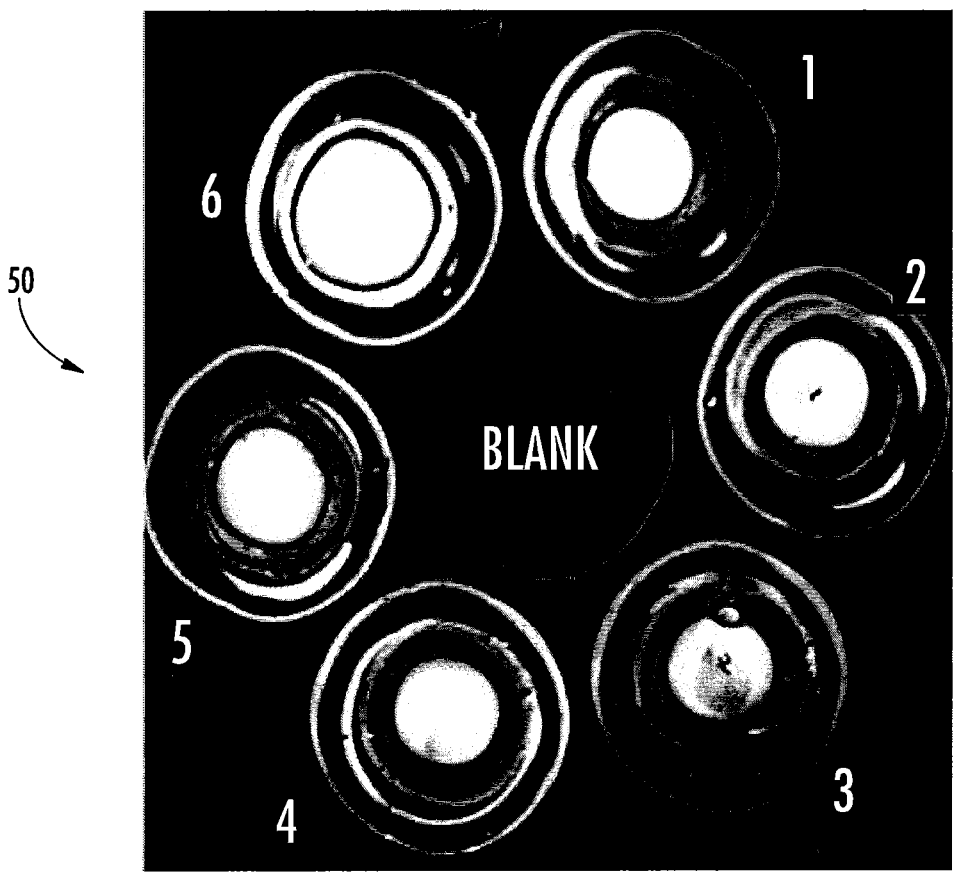
FIG. 7 is a digital fluorescence microscopy image showing a relatively strong signal from the intercalating dye for the wells of the device of FIGS. 2-3 containing amplified template molecules and virtually no signal from the blank reaction well in the center of the image according to some embodiments.

The system was tested using an rt-PCR chip such as the device 50 of FIGS. 2-3, in which the microfluidic portion 66 was constructed of PDMS, and the substrate 62 was constructed of glass. A bead set labeled with the forward PCR primer was mixed with a set of beads labeled with the reverse PCR primer in a 1/1 ratio in reaction wells 1-3 (FIG. 7). A 1-µL aliquot (containing ~10 µg of beads) from a set of beads with both the forward and reverse primer attached was added to each of wells 4-6 (FIG. 7). Genomic DNA was added to wells 1-6 in 10 µL volumes that delivered a total of 300-400 copies of template DNA to each well. Vacuum was applied to the waste until the wells were dry. Then 5 µL of master mix containing 0.28 units of Platinum Taq DNA polymerase (Invitrogen, Carlsbad, Calif.), 1× Platinum qPCRSupermix-UDG (Invitrogen, Carlsbad, Calif.), 1% Blocker BSA (Thermo Scientific, Rockford, Ill.) and 1×SYBR Green was added to each well. No additional primers were added. PDMS prepolymer was added to the waste reservoir to seal it. The device 50 was thermocycled from 66° C. to 95° C. for 60 cycles with a fluorescence image taken at the end of each cycle.

Figure 8:
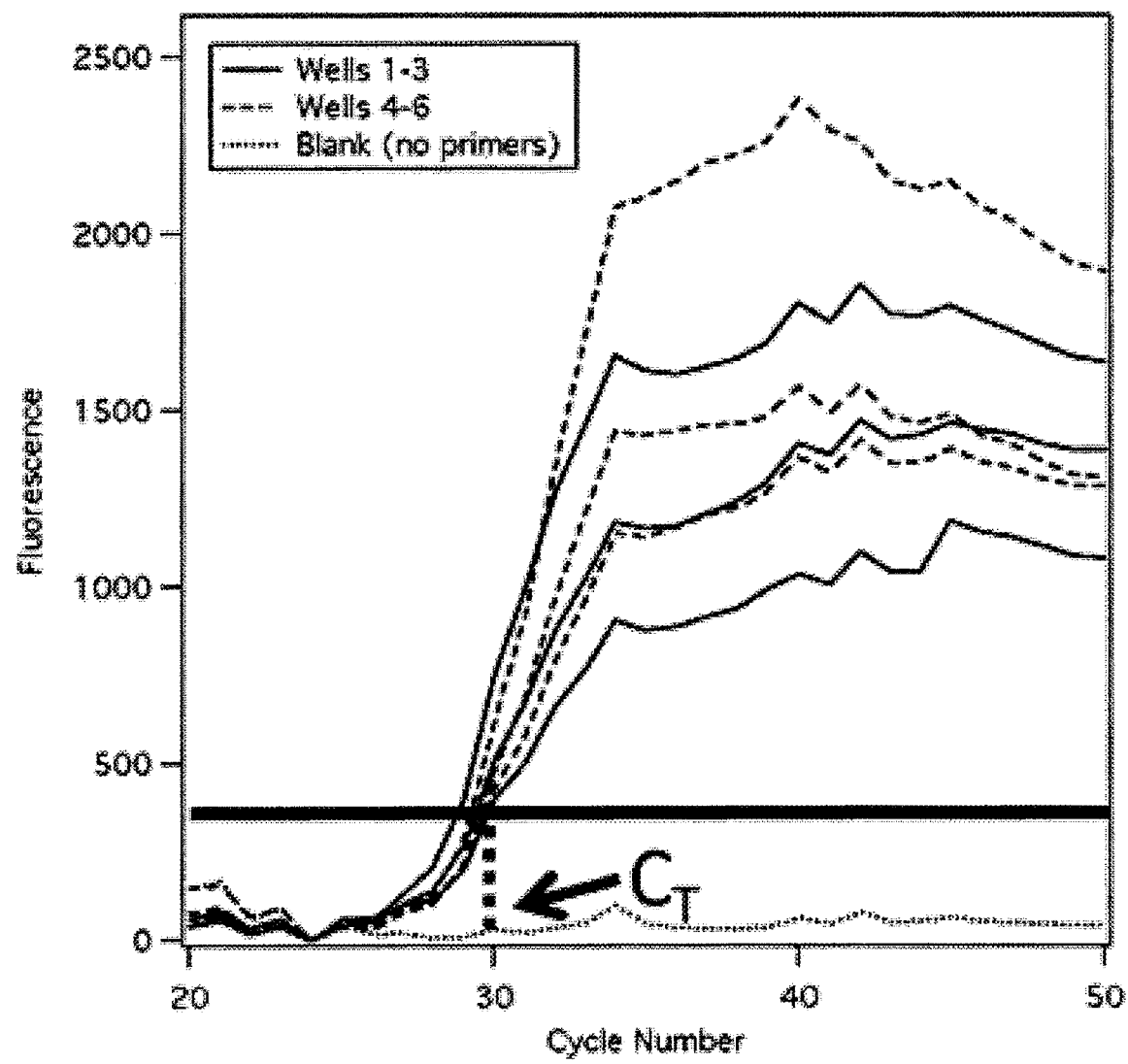
FIG. 8 is a graph of the fluorescence signal from each well in the device of FIGS. 2-3 plotted against the PCR cycle number for an rt-PCR experiment according to some embodiments.

FIG. 7 shows a background subtracted fluorescence microscopy image of the rt-PCR chip after the $50^{th}$ amplification cycle. A background subtracted set of images was used to calculate the average signal intensity from the SYBR Green intercalating dye. FIG. 8 is a graph of the amplification plots from each well. The cycle threshold ($C_T$) value where amplification is first evident is consistent for all reaction wells. This experiment demonstrates successful, reproducible on-chip rt-PCR can be performed using this technology. There was no discernible difference between a single bead set where a mix of the two primers were attached to the beads in a single reaction and a mix of two bead sets where only forward primers were attached to one bead set and only reverse primers were attached to another bead set. The preloaded biotinylated primers remained firmly attached to the beads during the sample cleanup step but were released into solution during PCR and successful amplification of template sequences was demonstrated.

Example 2

The device 200 of FIGS. 9-11 is made from a silicon substrate (substrate 220) and a glass substrate (substrate 210) using photolithography. Silicon wafers were coated with 5 nm of titanium (Ti) and 100 nm of gold (Au) using magnetron sputtering. The metalized wafer was coated with positive photoresist and patterned with photolithography so that arrays of either 50 μm×50 μm or 100 μm×100 μm square regions were exposed. The Au layer was removed from the exposed regions by treatment with aqua regia, leaving behind a layer of oxidized titanium that is very hydrophilic. The substrate was treated with 1-octadecanethiol to form a self-assembled monolayer on the Au surface only that is very hydrophobic. (Thiols such as 1-octadecanethiol form strong bonds with the Au, but not the oxidized titanium.)

Initial testing with the wafer side only (i.e. open and without glass) was performed by covering it with aqueous buffer containing dye. Mineral oil was gently flowed over the surface, and the majority of the aqueous phase was pushed off the gold-alkylthiol surface. Small droplets of aqueous buffer remained at the regions where the Au had been removed. The areas on the wafer covered by each droplet were well defined by the pattern, but droplet height (and therefore, volume) varied greatly.

A microfluidic device 200 with a patterned glass cover or substrate 210 was made to better control droplet size (FIGS. 9-11). Silicon wafers were fabricated as described above, but a photo-patterned border 1 mm wide and 9-25 μm high was made with an epoxy-based negative photoresist (KMPR1010, Microchem Corp., Newton, Mass.). A glass substrate was coated with 5 nm of Ti and 20 nm of Au. The Au was removed by photolithography to leave an array of hydrophilic squares (regions 214) complementary to corresponding squares (regions 224) on the silicon substrate 220 (FIG. 9). Vias or apertures 240 were drilled through the glass substrate 210 using abrasive powder blasting. The glass substrate 210 was aligned over the silicon substrate using a Finetech die bonder (FINEPLACER, Berlin, Germany) and permanently bonded using epoxy (LOCTITE Hysol E-120HP). FIG. 10 shows a schematic of the alignment, and FIG. 11 shows a diagram of the cross section of the chip. The metal film on the glass is mostly transparent at these thicknesses, making alignment and optical interrogation of the hydrophobic regions possible. After treatment in ethanol saturated with octadecanethiol for ≥12 hours, the chip was rinsed with pure ethanol and then stored dry.

Alternative methods for patterning the metal films on the substrates 210, 220 may be used to form hydrophilic and hydrophobic regions, including patterning of the substrate with a photoresist and then metal deposition with lift off and/or various sputtering techniques, such as argon ion sputtering. Additional techniques for forming hydrophilic and hydrophobic reasons will be readily apparent to those of skill in the art.

The chip was designed to include barriers or "lanes" 250 of negative photoresist to divide the array into separate regions so that the flow of immiscible phase could be better regulated (FIGS. 12-13). Fabrication was similar to that described above, and the lanes and outer border of the chip were patterned during the same step of photolithography. The Au was removed from areas where the photoresist was patterned as the alkylthiol treatment caused resist delamination from the Au after prolonged treatment. A solution of dye was added to fill the chip as previously described. Mineral oil was then added and vacuum was used to pull it through the chip. As can be seen in FIG. 14, droplets were isolated with mineral oil filling the interstitial space (defined by the hydrophobic regions on the substrates). A few small, stray droplets were observed but little to no bridging between wells was observed. The vast majority of droplets display similar and regular morphology.

Devices with 440 reaction regions measuring 100 μm×100 μm were fabricated using KMPR borders either 25 μm or 7.5 μm tall to form reaction volumes of either 250 pL or 75 pL. Higher density arrays incorporating 1,500 reaction wells (50 μm×50 μm pads with 9 μm tall KMPR) with volumes of 22.5 pL each within the same overall area were also fabricated and tested. FIGS. 15A-15C show the three chips filled with aqueous buffer containing fluorescein dye. Aqueous solutions were added as 2.5-5 μL droplets to one via, and vacuum was applied at the other via to fill the chip. After filling with buffer, mineral oil was added to the via and pulled through the chip. The mineral oil wet the Au/alkylthiol surface, forcing the aqueous solution from the bulk of the chip, leaving isolated droplets at the hydrophilic defined reaction regions. The filling/droplet isolation process can be very fast, typically requiring only ~2 minutes or less to define the isolated reaction wells.

Use of Chips in rt-PCR and Digital PCR Experiments

Figures 16A, 16B, 16C:
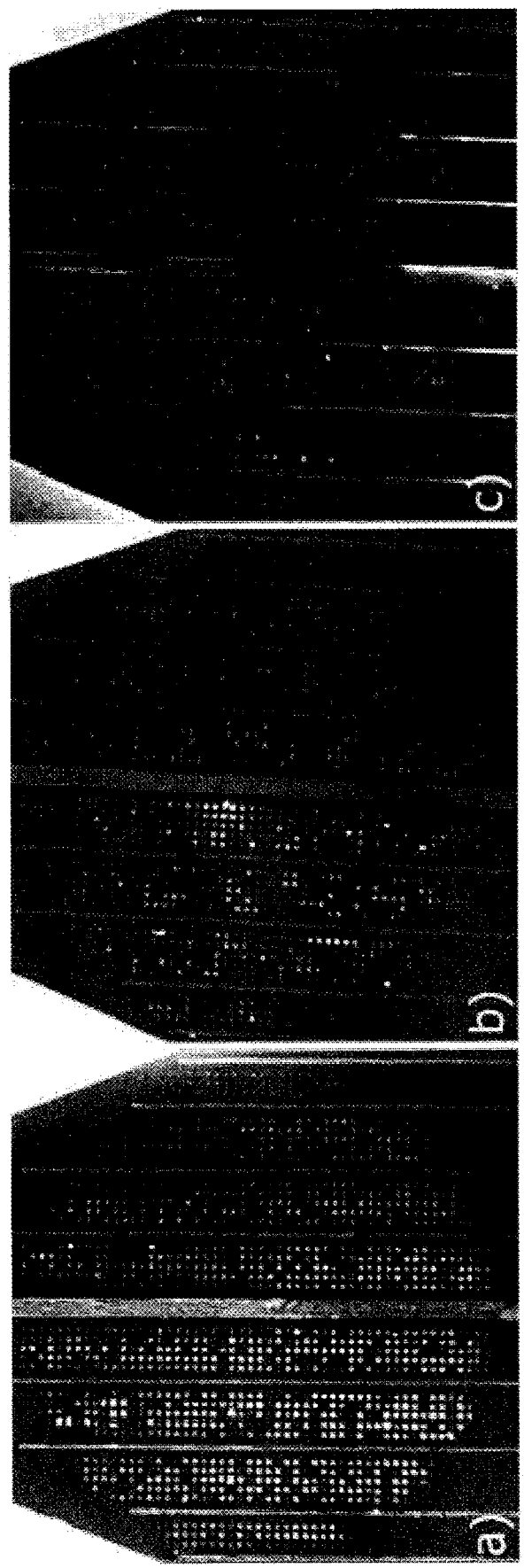
FIGS. 16A-16C are fluorescence images of digital PCR reactions in a microfluidic device according to some embodiments demonstrating single copy amplification in 22.5 pL reactions with 1500 reaction wells on each device with a nominal copy number/well of 0.7 (FIG. 16A), 0.2 (FIG. 16B), and 0.04 (FIG. 16C). Signals from cycles 20-25 were summed to improve the signal to noise for identifying positive wells.

Digital PCR using free solution primers at 250 nM was used to verify chip performance at the single-target-molecule level in 22.5 pL reactions (1,500 per chip). FIGS. 16A-16C show results from 0.7, 0.2, and 0.04 copies of template DNA/well (nominal concentration). Positive hits indicating that at least one target copy was present totaled ~1100 (73%), 360 (24%), and 140 (9%), respectively, out of a total of 1,500 wells. Assuming a Poisson distribution between wells, calculated concentrations of 1.3, 0.27, and 0.094 copies/well are reasonably close to the nominal concentrations, allowing for pipetting errors at submicroliter volumes during sample preparation. It should be noted that although the system has not been optimized for rapid thermocycling, detection of single copies of DNA was accomplished in less than 20 minutes. Shorter cycling times may be achieved with increased optimization of various parameters.

Demonstration of Bead-Loading using a Magnet for High Sampling Efficiency and High Bead Well Occupancy Some chip designs may use glass and silicon components to partition sample and reagents into isolated reaction wells, but these elements can be duplicated with analogous structures and surface chemistries in plastics, such as high-volume manufacturable, monolithic polymer devices.

Although gravity-based loading has been observed to result in >55% occupancy of 3.28-μm diameter magnetic primer-coated beads for the silicon and glass chip design, sampling efficiency from the total bead population was poor (<1%). To implement sampling of rare target sequences by hybridization to primers on the beads, sampling efficiency, defined here to mean the total number of beads loaded into bead wells divided by the total number of beads in the slurry incubated with the sample, should be as high as possible. Modifications to the bead well geometry and the use of a suitable blocking buffer was shown to significantly improve occupancy and bead sampling efficiency using magnetic loading. Magnetic manipulation of the beads can greatly speed delivery of the beads to the bead wells but can be problematic since the beads align along the magnetic field lines in chains that cause multiple loading in non-optimized geometries as noted in a recent paper in which magnetic loading was unsuccessful. [Kan, C. W. et al. Lab on a Chip, 2012, 12, 5, p. 977-985].

Figures 17A, 17B:
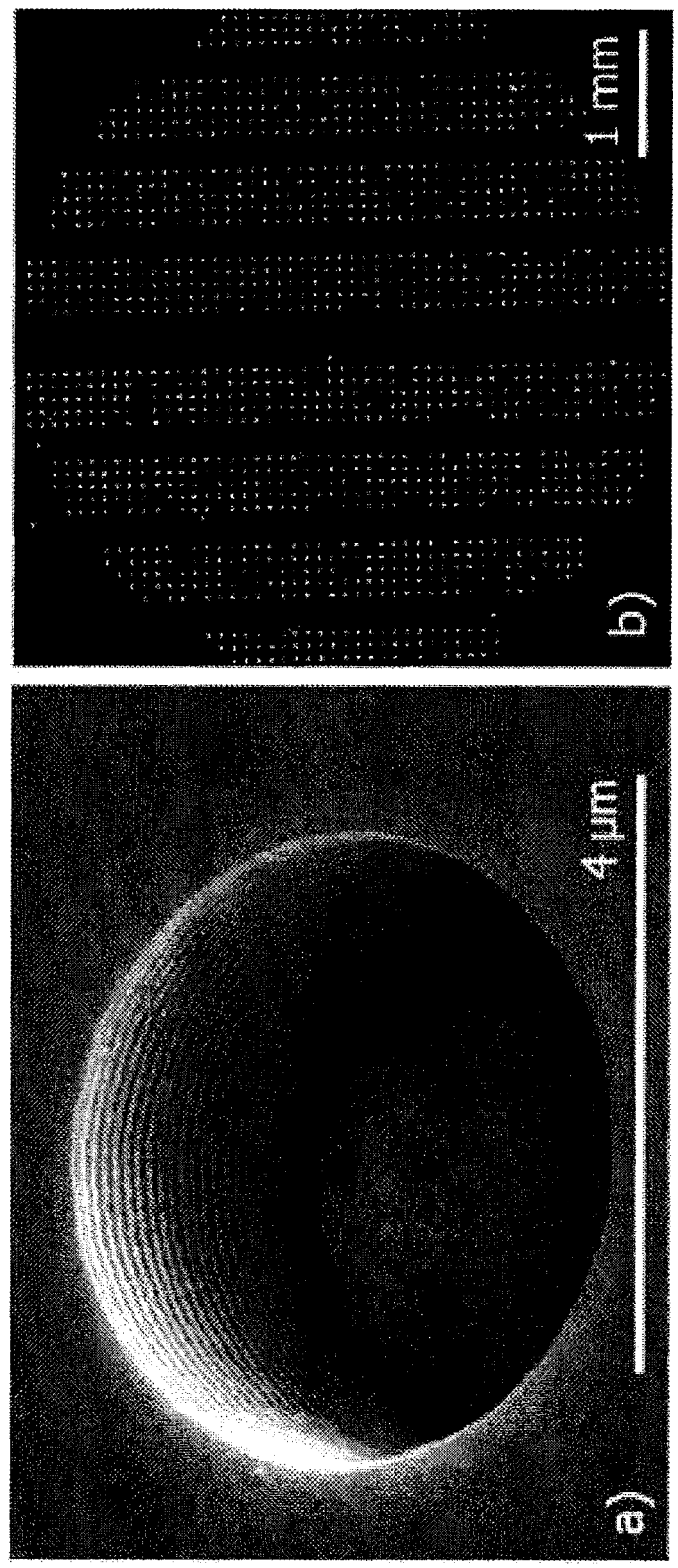
FIG. 17A is an SEM image of a loaded primer bead of 3.3 µm diameter loaded into a 4.15 µm diameter, 5.7 µm depth well according to some embodiments.
FIG. 17B is a fluorescence microscopy image of a device according to some embodiments illustrating greater than 90% bead occupancy in the wells.

DRIE was used to fabricate arrays of bead wells ranging in size from 2.5 to 5.4 μm in diameter with depths of 4.4, 5.7, and 7.0 μm into Si wafers. Wafers were cut into sections of 3-4 arrays each. Starting Block PBS buffer (Thermo Scientific) was used to block the arrays and prevent bead adsorption (currently, 0.5% BSA is used instead of Starting Block due to PCR inhibition problems observed on-chip). An aliquot of beads (~15,000) was placed at one side of the array, and a magnet was translated along the backside of the silicon to draw the beads over the array of bead wells while observing the beads with a microscope. After pulling the beads across a significant number of wells, the array was gently washed with deionized water, sputter coated with ~5 nm of Au/Pd, and imaged with SEM. Most arrays etched to 4.4 μm deep showed poor to moderate retention of beads after vigorous washing, but retention should be acceptable with more gentle washing. Arrays etched to 7.0 μm depth displayed many instances of double bead loading when examined by SEM. While good retention was seen for 3.5 μm diameter bead wells, multiple passes over the arrays were needed before appreciable loading was achieved. Arrays etched to a depth of 5.7 μm with diameters of 4.1 μm (FIGS. 17A-17B) loaded quickly and demonstrated good bead retention. Chips fabricated with bead wells of this geometry can be loaded with <15 k beads and typically show 80% to >90% bead occupancy after washing, yielding a sampling efficiency>8-10%. FIGS. 18A-18D show a series of images taken during the loading process. Beads are deposited into wells from the bright clump of fluorescent beads as it is moved over the array. Washing with buffer after loading removes most loose beads, leaving most wells loaded with single beads. Rare instances of double loading might be further reduced by decreasing the well depth to a value between 4.5 and 5.7 μm. It was observed that bead populations>10 k can be translocated much faster than smaller populations of beads; therefore, sampling efficiency may improve as the number of bead wells is increased. Increased optimization of the geometry of the magnet and automation of magnet movement may further improve occupancy and minimize loading time. In some embodiments, various ratios of beads to the wells or containment regions may be used to improve bead containment. For example, it is currently believed that, where a bead has a diameter d, and the solid support containment regions have a cylindrical shape having a diameter of 1.05d to 1.55d and a depth of 1.2d to 1.8d. This ratio may be particularly beneficial when using magnetic bead loading as described herein. In addition, this ratio may be used in any suitable bead array loading application or device, such as SiMoA.

Reducing Dimer Formation by Reducing Reaction Volume

Testing of biotinylated primer sets for the three targets was completed and the effect on primer dimer formation when the total volume of the master mix is divided into smaller, isolated reactions was explored. Massively parallel multiplexing-in-space may require a compatible thermocycling program for all primer sets. While significant primer dimer formation for nuc, *S. mutans*, and mecA primer sets is typically noted when performing PCR at low annealing temperatures in conventional volumes (5-10 μL) in polypropylene PCR tubes, reduced primer dimer formation on-chip in smaller volumes has also been observed. While it is possible that these observations may be due to differences in surface interactions, an alternative explanation may be that although the concentration of primers remains the same, the total number of primer molecules in a given reaction (and therefore the likelihood of amplifying a nonspecific interaction) decreases with reduction of the total primer population. Additionally, trace amounts of malformed primers that form during synthesis that are not removed during purification may also cause nonspecific amplification. Segmentation of the reaction such that the occurrence of these impurities in any given reaction is very low will reduce the instances of these nonspecific reactions. It is anticipated that the greatly reduced volumes used for single bead reactions (millions to a thousands of times less than a standard 10 μreaction) will allow the use of primer sets that are not currently compatible in conventional volume reactions because of primer dimer formation in some sets at low annealing temperatures. The ability to relax primer design constraints would greatly improve the accessibility of the technique and greatly accelerate reconfiguration to include new target sequences for the detection of emerging diseases. Often, dimer formation is a rare event, but when it occurs it is amplified and spreads throughout the entire reaction volume. When a given volume of PCR master mix is divided among many isolated wells, rare instances of dimer formation (or trace impurities) are effectively quarantined in one of many small reaction volumes, and the majority of the reactions remain unaffected.

TABLE 1

Reaction Volume and Dimer Occurrence

| | PCR Reaction Volume | |
| --- | --- | --- |
| Primer Set | 5 μL (n = 9) | 300 nL (n = 50) |
| *S. mutans* (16S rRNA) | 11% | 0% |
| *S. aureus* (nuc) | 22% | 0% |
| MRSA (mecA) | 11% | 2% |

Preliminary testing was performed to compare the degree of dimer formation in 5 μL reactions in PCR tubes with that observed in 300 nL on-chip reactions. Three stock master mixes were prepared, each containing 500 nM of a different primer set (Table 2), 1% Blocker BSA, 1× Platinum Quantitative PCR SuperMix-UDG, 1×SYBR Green I, and 0.0625 units/μL, additional Platinum Taq DNA polymerase. Nine aliquots (5 μL) were then dispensed into propylene PCR tubes and thermocycled for 60 cycles with a 60° C. annealing temperature. After thermocycling, the PCR mixes were analyzed using capillary gel electrophoresis on an Agilent Bioanalyzer 2100 with a DNA 1000 chip. Dimer formation was observed in 11-22% of these reactions. Fifty on-chip reactions (300 nL each) were prepared from master mixes formulated as above and thermocycled on-chip using rt-PCR. Only one of the on-chip reactions showed primer dimers in the SYBR Green I fluorescence signal. Positive controls for *S. mutans* 16S rRNA and mecA sequences indicated successful amplification for 11/11 reactions, respectively.

Hybridization with Primer-Functionalized Beads

Figure 20:
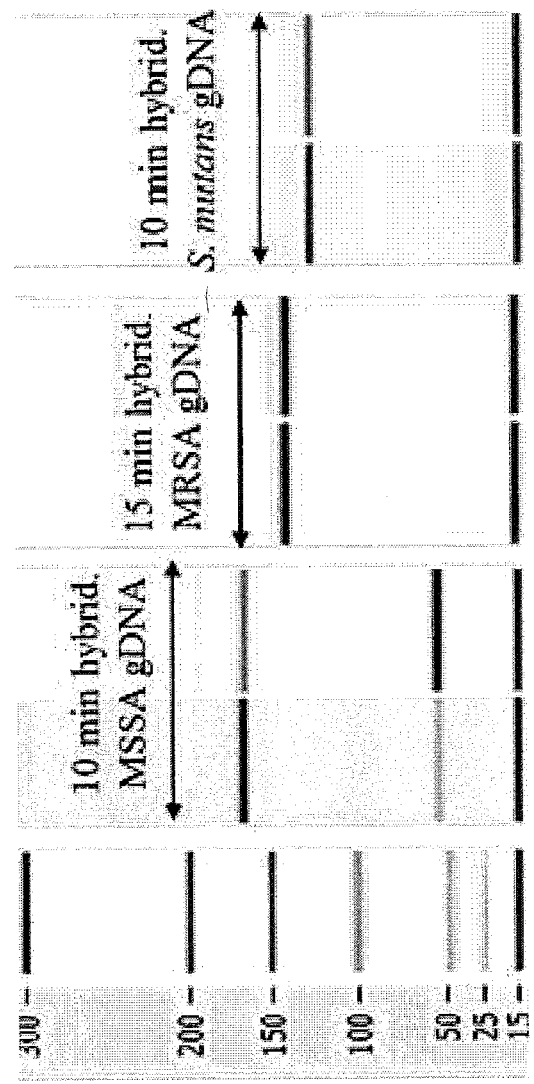
FIG. 20 is a graph of the amplification in 5 µL reactions after bulk bead-based capture of target DNA according to some embodiments.

Preliminary investigations into the ability of the primer-labeled beads to sample DNA from dilute solution using bulk beads and standard PCR have been performed. Target gDNA (~350 copies/μL) was digested for 15 min at 37° C. with restriction enzymes (such as EcoRV, Bpu10I, and SfaNI) to cut the DNA near the targeted region. The digestion was then heated to 95° C. for 5 min to denature the DNA. Ten μL of this digest (~3,500 copies) was then incubated for 10-15 minutes with 5 μL of bead slurry (~25 μg beads). Three, 15 μL wash steps were performed with PCR buffer (w/o polymerase). A 1.5 μL aliquot was then added to a PCR master mix to form a 5 μL reaction that was thermocycled 60 times. Example electropherograms plotted as gels are shown in FIG. 20. If a carryover of 0.5 μL between wash steps is assumed, then only ~0.013 copies of target DNA was transferred in the liquid phase. Therefore, these preliminary results indicate that the beads are capturing DNA in some manner. The mechanism of DNA attachment to the beads may be specific hybridization or nonspecific adsorption. While hybridization is preferred for efficient sampling and the lowest possible limits of detection, some degree of nonspecific adsorption is not likely to be detrimental to the assay since the identity of the target is determined by PCR amplification.

Example 3

Figure 21C:
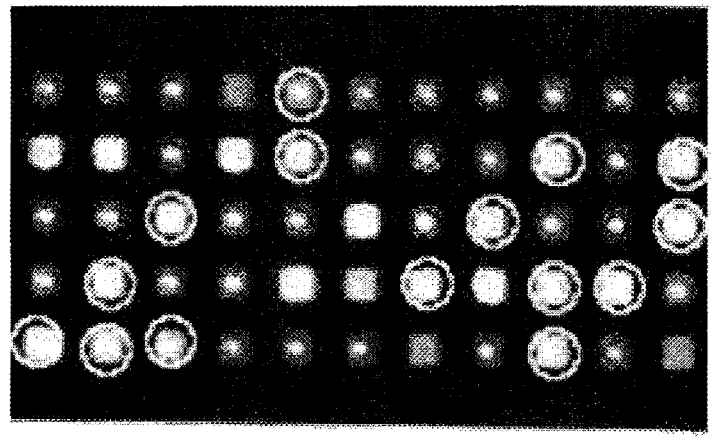
FIGS. 21A-21C are images of sections of an array from a microfluidic device according to some embodiments after 30 cycles of PCR amplification showing an increase in SYBR green fluorescence in positive wells for three different primer sets encoded with with color fluorescence according to some embodiments.
Figure 21B:
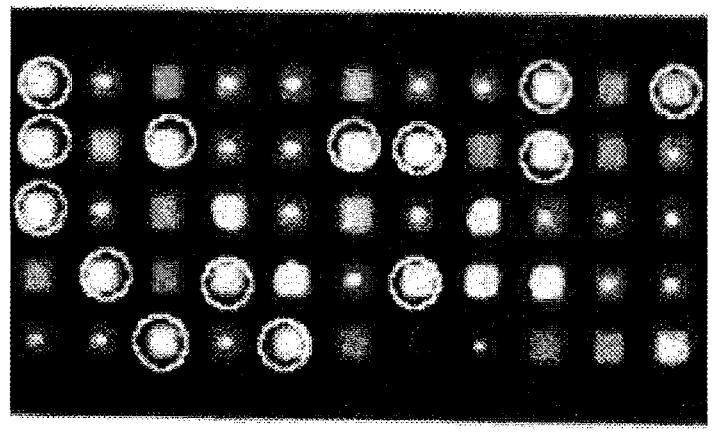
Figure 21A:
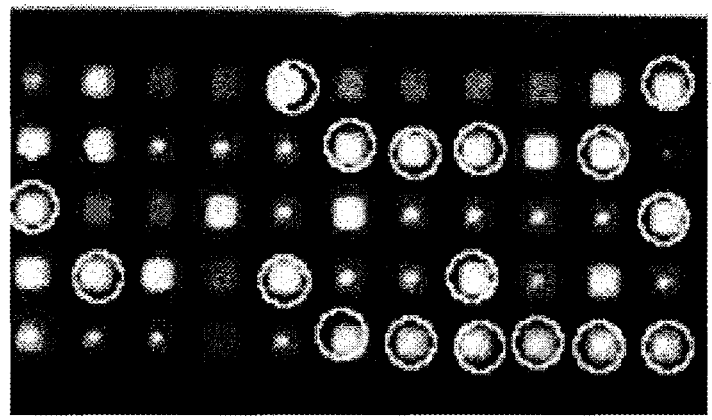

FIGS. 21A-21C show a representative section from an example encoded bead-based assay for the detection of MRSA by multiple genetic markers (nuc and mecA, with *S. mutans* as a negative control).

Figure 19B:
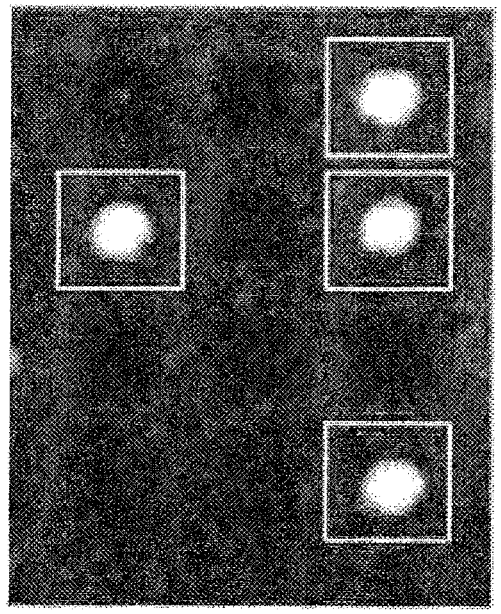
FIGS. 19A-19C are decoded images of the same twelve reaction wells imaged with different fluorescence filter sets such that beads of interest are highlighted with white squares according to some embodiments.
Figure 19A:
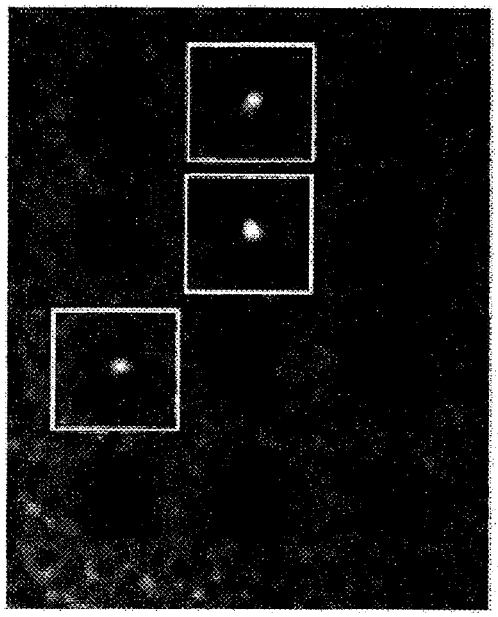

Three aliquots of streptavidin-coated beads (Bangs Laboratories, Inc., product #PMS3N/10098) were placed into separate 200 μL PCR-grade polypropylene tubes. A different set of forward and reverse 5'-biotinylated primers were incubated with each aliquot so that one aliquot contained primers for nuc gene found in *Staphylococcus aureus* gDNA, another contained primers for the mecA gene found in Methicillin-resistant *S. aureus* (MRSA), and the third contained primers for *Streptococcus mutans* gDNA. After incubation, the beads were washed with buffer to remove any primers not bonded to the bead surface. Beads with primers for the mecA gene were then incubated with biotin-labeled Qdot® 605 nanocrystals (Invitrogen, Carlsbad, Calif.), and beads with primers for *S. mutans* gDNA were incubated with biotin-labeled Qdot® 655 nanocrystals (Invitrogen) for encoding purposes. Beads with primers for the nuc gene found in *S. aureus* were incubated in buffer only. After incubation, the bead sets were washed with buffer to remove any unbound biotin-labeled Qdot nanocrystals. In this manner, a rudimentary encoding scheme was implemented; however, encoding is not limited to this method and can be done using the various other methods described herein. Aliquots of beads from each set were then mixed together to form a slurry containing all three bead types. Bead type was readily discernible using fluorescence microscopy by monitoring the emission from the Qdot605, Qdot655, or autofluorescence of the unlabeled beads (FIGS. 19A-19C).

A microfluidic chip such as the device 200 in FIGS. 9-11 was used to isolate individual beads in separate reaction wells (~22.5 pL each). Briefly, silicon wafers were coated with 5 nm of titanium and 100 nm of gold using magnetron sputtering. Glass substrates were also coated with 5 nm of titanium and 20 nm of gold. Photolithographic patterning was used on both the silicon wafers and glass substrates to form an array of 1,500 reaction regions, each region defined as a square measuring 50 μm on a side, where the gold was removed leaving a hydrophilic oxide surface. A single bead well measuring ~4.1 μm in diameter and 5.7 μm deep was etched into the center of each reaction region using photolithography and deep reactive ion etching. A layer of negative photoresist (KMPR1010, MicroChem Corp., Newton, Mass.) was patterned onto the surface of the silicon wafer to form a pattern of channels and walls ~9 μm tall. After fabricating holes in the glass substrate for the addition of reagents, it was aligned over the silicon wafer so that the hydrophilic oxide pattern complemented that on the silicon wafer. The two were then bonded using epoxy so that a gap of ~9 μm separated the glass substrate from the silicon wafer. The device was filled with a saturated solution of 1-octadecanethiol in pure ethanol and left for >12 hours so that a self-assembled monolayer of the alkylthiol formed on the gold surfaces of the glass and silicon substrates.

The microfluidic device was filled with buffer, and a small amount of the mixture containing the three different bead types was then loaded into the device. A magnet was applied to the outside of the device so that the magnetic beads were pulled over the array of bead wells etched into a silicon substrate. A single bead was observed to load in ~80% to greater than 90% of the bead wells. The array was washed with buffer to remove loose beads. The array was then imaged by fluorescence microscopy to determine the type and location of each loaded bead.

PCR master mix was prepared with 1× Platinum qPCR-Supermix-UDG and 0.11 units/μL additional Platinum Taq DNA polymerase (Invitrogen, Carlsbad, Calif.), 0.55% Blocker BSA (Thermo Scientific, Rockford, Ill.), and 1×SYBR Green I (Invitrogen, Carlsbad, Calif.), and approximately 15 copies of MRSA gDNA (ATCC #700699D-5) per 25 pL reaction. The master mix was then loaded into the microfluidic device so that it completely filled the gap between the glass and silicon. Mineral oil was then added to the device and transported across the well array by vacuum. The mineral oil preferentially wet the alkylthiol-treated gold surfaces, leaving behind isolated ~25 pL aqueous droplets sandwiched between the exposed hydrophilic oxide surfaces.

The chip was placed onto a thermocycling stage where it was heated to 50° C. for 12 seconds, 90° C. for 120 s, and then 30 cycles of 90° C. for 5 s and 60° C. for 30 s. The array was imaged after every cycle to monitor fluorescence emission from the SYBR Green I intercalating dye. Approximately 94% of the reaction wells containing beads identified as those carrying primers for nuc gene found in *S. aureus* gDNA showed evidence of PCR amplification, as did ~94% of reaction wells containing beads carrying primers for the mecA gene found in Methicillin-resistant *S. aureus* (MRSA). Only ~6% of wells identified as containing primers for *S. mutans* gDNA showed a positive result. Approximately 2% of the bead wells were identified as containing both one MRSA primer bead and one mutans primer bead. It is likely that some double loading of beads carrying primers for the nuc gene occurred, causing the false positives seen for *S. mutans* primer sets, but this could not be readily discerned from the weak autofluorescence signal from the polystyrene shell of the bead (as no encoding dye was used with this set). It can be anticipated that further optimization of bead well geometries and more highly refined encoding methods can be readily implemented to reduce false positive signals.

Figure 19D:
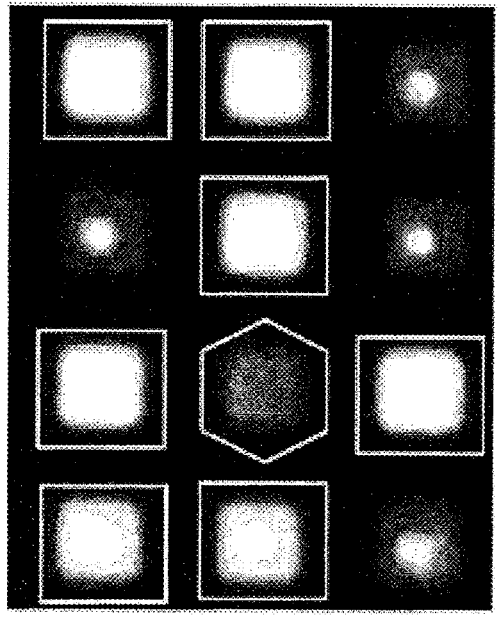
FIG. 19D is an assay image showing positive results for mecA and nuc genes.
Figure 19C:
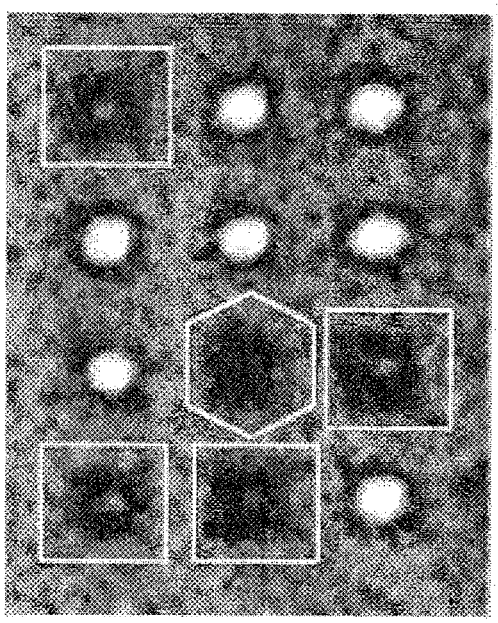

A small region of a chip is shown in fluorescence microscopy images of 12 reaction wells with ~25 pL volume each are shown in FIGS. 19A-19D. FIG. 19A is an encoding image with 365/10 nm ex. and 605/55 nm em. Three beads labeled with Qdot 605 and primers for the mecA gene found in MRSA gDNA are highlighted with white squares. FIG. 19B shows an encoding image at 445/50 nm ex. and 665/30 nm em. Four beads labeled with Qdot 655 and primers for *S. mutans* gDNA are highlighted with white squares. FIG. 19C shows a third encoding image at 556/20 nm ex. and 620/60 nm em. All bead sets autofluoresce weakly at these wavelengths, and both Qdot 605 and Qdot 655 labeled beads fluoresce brightly. Beads without Qdot labels (highlighted with white squares) carry primers for the nuc gene found in *S. aureus* gDNA. An empty bead well is highlighted with a white hexagon. FIG. 19D shows an assay image at 470/40 nm ex. and 525/50 nm em. after thermocycling 30 times. SYBR Green I fluorescence in the presence of significant amounts of double stranded DNA can be readily detected, indicating detection of the analyte. Reaction wells outlined with squares showed large increases in signal, whereas the other reaction wells only showed bead autofluorescence or a weak signal from non-intercalated SYBR Green I, similar to that shown by the well that contained no primers (white hexagon).

TABLE 2

Results from whole chip

|  | nuc-MSSA | mecA-MRSA | S. Mutans |
|---|---|---|---|
| Total Beads | ~6,000 | ~6,000 | ~6,000 |
| Loaded Beads | 174 | 440 | 561 |
| Active Wells | 164 | 413 | 34 |
| Negative Wells | 10 | 27 | 527 |
| Double-Loaded | ND | 13 | 13 |

Accordingly, PCR probes (for example Taqman and molecular beacon probes, among others) can improve the specificity of PCR, and these can be easily attached to the beads along with the primers if the probes are biotinylated or otherwise functionalized for attachment to a solid surface. As the beads are deterministically loaded into the reaction wells, a single detection fluorophore may be used for all probe sets. Additional optimization may be performed if probes are incorporated. PCR reactions that do not require probes can be used on the same chip with reactions that use probes if similar thermocycling and master mix conditions are used for both types of reaction. In some cases, universal primers could be added to the master mix in free solution and specific probes could be attached to the beads in place of specific primer sets.

While some embodiments of the invention uses a solid-phase extraction membrane 68 (FIGS. 2-3) to purify the DNA before PCR, other implementations of the device can use direct hybridization of target DNA to its sequence-specific primers bonded to the microbeads. When the bead mixture is incubated with analyte DNA or cDNA, the primers attached to the beads will act as hybridization probes, capturing and purifying the sequence specific to that bead. Primers can be designed to optimize these hybridization events by controlling their length and sequence or the addition of novel nucleobases. Interfering components of the sample matrix (extraneous gDNA, RNA, cell membrane components, etc.) can be washed away, leaving purified target DNA hybridized to the primers bonded to the beads.

Some embodiments may also be implemented in a digital PCR format where many reaction wells can contain one or more beads or surfaces of the same set labeled with primers. Quantification may then based upon endpoint detection. Quantification of targets using isothermal amplification may also be accomplished in a manner similar to digital PCR approaches.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of conducting a reaction using the solid supports in a microfluidic device, the microfluidic device comprising: a substrate having a plurality of solid support containment regions that are sized and configured to capture a plurality of solid supports having a diameter d, wherein each of the solid supports has a reagent attached via a labile reagent/support bond and the reagent is configured to be cleaved from the support via a cleaving operation, and wherein the reagent comprises a DNA primer or probe for a PCR reaction, and the solid support containment regions have a cylindrical shape having a diameter of 1.05d to 1.55d and a depth of 1.2d to 1.8d, the solid supports comprising magnetic solid supports, the method comprising:

loading the solid supports in the plurality of solid support containment regions by applying a magnet or magnetic field, wherein the magnetic field has a field component parallel to the substrate and is applied translationally across the substrate to move the solid supports across the substrate and into the plurality of solid support containment regions;

washing the plurality of solid support containment regions with a blocking buffer configured to reduce or prevent bead adsorption, multiple bead loading, and chain formation; and loading a sample and a PCR master mix in the plurality of solid support containment regions; and after applying the magnetic field to move the solid supports across the substrate and into the containment regions and loading the sample and the PCR master mix, flowing a sealing fluid comprising oil, liquid polymer, or fluorocarbon liquid over the plurality of solid support containment regions to seal the plurality of containment regions, wherein the sealing fluid isolates reagents in the plurality of solid support containment regions and fluidically isolates each of the plurality of solid support containment regions during a reaction.

2. The method of claim 1, wherein the solid supports comprise super paramagnetic supports.

3. The method of claim 1, wherein the substrate comprises channels and an array of the containment regions, and loading the solid supports comprises moving at least one of the solid supports across at least one of the channels and into one of the containment regions.

4. The method of claim 1, the method further comprising: performing a cleaving operation to release the reagent into a solution in the plurality of containment regions.

5. The method of claim 1, wherein the plurality of solid supports comprises at least a first plurality of solid supports having a first reagent attached thereto and a second plurality of solid supports having a second reagent attached thereto, wherein the first and second plurality of solid supports further comprise respective first and second markers configured to identify a property of the solid support and/or reagent.

6. The method of claim 5, further comprising decoding the device by identifying whether each of the plurality of solid support containment regions is occupied by the first plurality of solid supports or the second plurality of solid supports.

7. The method of claim 6, wherein decoding the device comprises identifying the first and second markers of the plurality of solid supports.

8. The method of claim 1, wherein the solid supports are a polymer, magnetic material, or a combination thereof.

9. The method of claim 1, wherein the solid supports comprise beads about 3.3 µm in diameter.

10. The method of claim 4, wherein the cleaving operation is an addition of a chemical, the addition of an enzyme, application of an electric potential, and/or an application of light, or ionizing radiation to the reagent/support bond.

11. The method of claim 4, wherein the cleaving operation comprises a thermal operation.

12. The method of claim 4, wherein the reagent comprises a nucleic acid sequence for a nucleic acid transcription and/or amplification reaction.

13. A method of conducting a reaction using the solid supports in a microfluidic device, the microfluidic device comprising: a substrate having a plurality of solid support containment regions that are sized and configured to capture a plurality of solid supports having a diameter d, wherein each of the solid supports has a reagent attached via a labile reagent/support bond and the reagent is configured to be cleaved from the support via a cleaving operation, and wherein the reagent comprises a DNA primer or probe for a PCR reaction, and the solid support containment regions have a cylindrical shape having a diameter of 1.05d to 1.55d and a depth of 1.2d to 1.8d, the solid supports comprising magnetic solid supports, the method comprising:

loading the solid supports in the plurality of solid support containment regions by applying a magnet or magnetic field, wherein the magnet or magnetic field is applied to move the solid supports across the substrate and into the plurality of solid support containment regions, wherein the plurality of solid support containment regions and the plurality of solid supports are sized and configured such that a single one of the plurality of solid supports is retained in a corresponding single one of the plurality of solid support containment regions; and loading a sample and a PCR master mix in the plurality of solid support containment regions; and after applying the magnetic field to move the solid supports across the substrate and into the containment regions and loading the sample and the PCR master mix, flowing a sealing fluid comprising oil, liquid polymer, or fluorocarbon liquid over the plurality of solid support containment regions to seal the plurality of containment regions, wherein the sealing fluid isolates reagents in the plurality of solid support containment regions and fluidically isolates each of the plurality of solid support containment regions during a reaction.

14. The method of claim 1, wherein the buffer comprises bovine serum albumin (BSA).

\* \* \* \* \*